(12) United States Patent
Hejazi et al.

(10) Patent No.: US 12,392,027 B2
(45) Date of Patent: Aug. 19, 2025

(54) METHOD OF FORMING A DIAMOND COATING ON A CARBON MATERIAL

(71) Applicants: The University of Melbourne, Melbourne (AU); THE NATIONAL VISION RESEARCH INSTITUTE OF AUSTRALIA, AUSTRALIAN COLLEGE OF OPTOMETRY, Carlton (AU)

(72) Inventors: Maryam Alsadat Hejazi, Melbourne (AU); David John Garrett, Melbourne (AU); Alastair Douglas Stacey, Melbourne (AU); Nicholas Vincent Apollo, Melbourne (AU); Kumaravelu Ganesan, Melbourne (AU); Matias Ismael Maturana, Melbourne (AU); Steven Prawer, Melbourne (AU); Wei Tong, Melbourne (AU); Melanie Elisabeth Maria Stamp, Melbourne (AU); Michael Ibbotson, Carlton (AU)

(73) Assignees: The University of Melbourne, Victoria (AU); THE NATIONAL VISION RESEARCH INSTITUTE OF AUSTRALIA, AUSTRALIAN COLLEGE OF OPTOMETRY, Carlton (AU)

( * ) Notice: Subject to any disclaimer, the term of this patent is extended or adjusted under 35 U.S.C. 154(b) by 861 days.

(21) Appl. No.: 17/310,555

(22) PCT Filed: Feb. 11, 2020

(86) PCT No.: PCT/AU2020/050114
§ 371 (c)(1),
(2) Date: Aug. 10, 2021

(87) PCT Pub. No.: WO2020/163909
PCT Pub. Date: Aug. 20, 2020

(65) Prior Publication Data
US 2022/0127720 A1    Apr. 28, 2022

(30) Foreign Application Priority Data

Feb. 11, 2019 (AU) ............................... 2019900435

(51) Int. Cl.
*C23C 16/00* (2006.01)
*A61B 5/1468* (2006.01)
(Continued)

(52) U.S. Cl.
CPC .......... *C23C 16/274* (2013.01); *A61B 5/1468* (2013.01); *A61N 1/0543* (2013.01);
(Continued)

(58) Field of Classification Search
CPC ..................................................... C23C 16/00
See application file for complete search history.

(56) References Cited

U.S. PATENT DOCUMENTS

| | | | |
|---|---|---|---|
| 9,756,797 | B2 | 9/2017 | Sarver et al. |
| 2004/0145379 | A1 | 7/2004 | Buss |

(Continued)

FOREIGN PATENT DOCUMENTS

| | | |
|---|---|---|
| CN | 104451596 A | 3/2015 |
| CN | 106684045 B | 1/2019 |

(Continued)

OTHER PUBLICATIONS

"3D-nanostructured boron-doped diamond for microelectrode array neural interfacing", Gaelle Piret, Clement Hebert, Jean-Paul Mazellier, Lionel Rousseau, Biomaterials, vol. 53, pp. 173-183, (Year: 2015).*

(Continued)

*Primary Examiner* — Gordon Baldwin
*Assistant Examiner* — Mohammad Mayy
(74) *Attorney, Agent, or Firm* — Knobbe Martens Olson & Bear LLP

(57) ABSTRACT

Disclosed is a method of forming a conductive diamond layer on a surface of a carbon fibre substrate that is used as (Continued)

a component of an electrode for neural stimulation and/or electrochemical sensing. The method comprises functionalising at least a portion of the surface with a functionalising agent to facilitate coating the surface with the conductive diamond layer. The method also comprises providing a diamond precursor and depositing the diamond precursor over the functionalising agent to form the conductive diamond layer. The disclosure also relates to an electrode that is used as a component of an electrode for neural stimulation and/or electrochemical sensing.

15 Claims, 14 Drawing Sheets

(51) Int. Cl.
| | |
|---|---|
| A61N 1/05 | (2006.01) |
| C01B 32/05 | (2017.01) |
| C23C 16/02 | (2006.01) |
| C23C 16/04 | (2006.01) |
| C23C 16/27 | (2006.01) |
| C23C 16/54 | (2006.01) |
| C30B 25/04 | (2006.01) |
| C30B 25/18 | (2006.01) |
| C30B 29/04 | (2006.01) |
| D06M 11/74 | (2006.01) |
| D06M 23/06 | (2006.01) |
| H01B 1/04 | (2006.01) |
| A61N 1/36 | (2006.01) |
| D06M 101/40 | (2006.01) |

(52) U.S. Cl.
CPC .......... *C01B 32/05* (2017.08); *C23C 16/0272* (2013.01); *C23C 16/042* (2013.01); *C23C 16/545* (2013.01); *C30B 25/04* (2013.01); *C30B 25/18* (2013.01); *C30B 29/04* (2013.01); *D06M 11/74* (2013.01); *D06M 23/06* (2013.01); *H01B 1/04* (2013.01); *A61B 2562/0285* (2013.01); *A61N 1/36046* (2013.01); *C01P 2002/82* (2013.01); *C01P 2002/85* (2013.01); *C01P 2004/02* (2013.01); *C01P 2004/03* (2013.01); *C01P 2004/80* (2013.01); *C01P 2006/40* (2013.01); *D06M 2101/40* (2013.01)

(56) References Cited

U.S. PATENT DOCUMENTS

| | | | |
|---|---|---|---|
| 2006/0190219 | A1 | 8/2006 | Froyland et al. |
| 2006/0265342 | A1 | 11/2006 | Froyland et al. |
| 2008/0091307 | A1 | 4/2008 | Dansereau et al. |
| 2013/0262045 | A1 | 10/2013 | Darby, Jr. et al. |
| 2015/0250421 | A1 | 9/2015 | Arumegam et al. |
| 2018/0348714 | A1 | 12/2018 | LaRue |
| 2018/0368339 | A1 | 12/2018 | van der Lee |
| 2020/0110170 | A1 | 4/2020 | Chandra et al. |
| 2021/0208305 | A1 | 7/2021 | Rubinstein et al. |
| 2021/0364462 | A1 | 11/2021 | Orangi et al. |

FOREIGN PATENT DOCUMENTS

| | | |
|---|---|---|
| EP | 2896783 A1 | 7/2015 |
| ES | 2377394 A1 | 3/2012 |
| WO | WO 95/06881 A1 | 3/1995 |
| WO | 2013/113493 A1 | 8/2013 |
| WO | WO 2018/107245 A1 | 6/2018 |

OTHER PUBLICATIONS

"Effect of nitrogen incorporation on electrical properties of boron-doped diamond films", S. Sonoda, J. H. Won, H. Yagi, A. Hatta, T. Ito, and A. Hiraki, Appl. Phys. Lett. 70 (19), May 12, 1997.*
"Hybrid diamond/ carbon fiber microelectrodes enable multimodal electrical/chemical neural interfacing" Maryam A. Hejazia, David J . Garrett, Biomaterials 230, 119648, (Year: 2020).*
A novel facile synthesis and characterization of heterostructures composed of carbon nanotubes and few-layer molybdenum disulfide sheets containing organic interlayers, Natalia D. Lenenko, Superlattices and Microstructures 76, 26-35 (Year: 2014).*
"Nanodiamond-Assisted Dispersion of Carbon Nanotubes and Hybrid Nanocarbon-Based Composites", S. Ciftan Hens, Nanoscience and Nanotechnology Letters, vol. 3, 1-8, (Year: 2011).*
"Boosting the electrochemical properties of diamond electrodes using carbon nanotube scaffolds" Clement Hebert, Carbon, 71, 27-33, (Year: 2014).*
The extended European search report issued for European Patent Application No. 20756566.4, dated Mar. 17, 2022 in 18 pages.
Luong et al., "Boron-doped diamond electrode: synthesis, characterization, functionalization and analytical applications"; The Analyst, vol. 134, No. 10, pp. 1965-1979, Jan. 1, 2009.
Allen et al., "Crop evapotranspiration—Guidelines for computing crop water requirements"; FAO Irrigation and drainage paper 56, Rome (1998).
Azzamouri et al., "Scheduling of open-pit phosphate mine extraction"; International Journal of Production Research, Feb. 2018, 22pgs.
Bai et al., "Automatic generation of feasible mining pushbacks for open pit strategic plannin"; The Journal of the Southern African Institute of Mining and Metallurgy; May 2018, vol. 118, pp. 515-530.
Gorr, "Neural networks in forecasting: Special section Research prospective on neural network forecasting"; International Journal of Forecasting 10; pp. 1-4 (1994).
Kaastra et al., "Designing a neural network for forecasting financial and economic time series"; Neurocomputing 10; pp. 215-236 (1996).
Morales et al., "An Integer Linear Programming Model for Optimizing Open Pit Ramp Design"; Delphos Mine Planning Laboratory, Department of Mining Engineering, Faculty of Physical and Mathematics Sciences, University of Chile, Chile; Advanced Mining Technology Center, University of Chile, Chile; pp. 11-19-11-16.
Moré, "The Levenberg-Marquardt Algorithm: Implementation and Theory"; Work performed under hte auspices of the U.S. Energy Research and Development Administration; pp. 105-116 (1977).
Thompson, "Test of an Innovation Stochastic Design System on an Open Pit"; Department of Mining Engineering, Queen's University, Canada; 2010, in 175pgs. [Uploaded in 3 parts].
Wigneron et al., "Estimating root zone soil moisture from surface soil moisture data adn soil-vegetation-atomosphere transfer modeling"; Water Recourses Research, vol. 35, No. 12, pp. 3735-3745, Dec. 1999.
Zhang, "Time series forecasting using a hybrid ARIMA and neural network model"; Neurocomputing 50, pp. 159-175 (2003).
Zhang et al., "Neural network forecasting for seasonal and trend time series"; Computing, Artificial Intelligence and Information Technology; European Journal of Operational Research 160, pp. 501-514 (2005).
International Preliminary Report on Patentability for International Application No. PCT/AU2019/050529, dated May 25, 2020 in 23 pages.
International Search Report issued for International Patent Application No. PCT/AU2020/050079, dated Apr. 17, 2020 in 5 pages.
International Search Report issued for International Patent Application No. PCT/AU2020/050114, dated Mar. 19, 2020 in 3 pages.
Allongue et al., "Covalent Modification of Carbon Surfaces by Aryl Radicals Generated from the Electrochemical Reduction of Diazonium Salts"; Journal of American Chemical Society, vol. 119, No. 1, pp. 201-207 (1997).
Bendali et al., "Synthetic 3D diamond-based electrodes for flexible retinal neuroprostheses: Model, production and in vivo biocompatibility"; Biomaterials, Elsevier, 67, pp. 73-83 (2015).

(56) References Cited

OTHER PUBLICATIONS

Girard et al., "Electrostatic Grafting of Diamond Nanoparticles: A Versatile Route to Nanocrystalline Diamond Thin Films"; ACS Applied Materials & INterfaces, vol. 1, No. 12, pp. 2738-2746 (2009).

Hebert et al., "Boosting the electrochemical properties of diamond electrodes using carbon nanotube scaffolds"; Carbon, 71, pp. 27-33 (2014).

Hopper et al., "Photochemically modified diamond-like carbon surfaces for neural interfaces"; Materials Science and Engineering: C, vol. 58, pp. 1199-1206, Jan. 1, 2016.

Liu et al., "Fluorinated Nanodiamond as a Wet Chemistry Precursor for Diamond Coatings Covalently Bonded to Glass Surface"; Journal of American Chemical Society, 127, pp. 3712-3713 (2005).

Pinheiro et al., "Methods to grow porous diamond film doped with boron and nitrogen by deposition on carbon nanotubes"; Diamond & Related Materials 65, pp. 198-203 (2016).

Silva et al., "Thin-film nanocomposites of BDD/CNT deposited on carbon fiber"; Diamond & Related Materials, 75 pp. 116-122 (2017).

\* cited by examiner

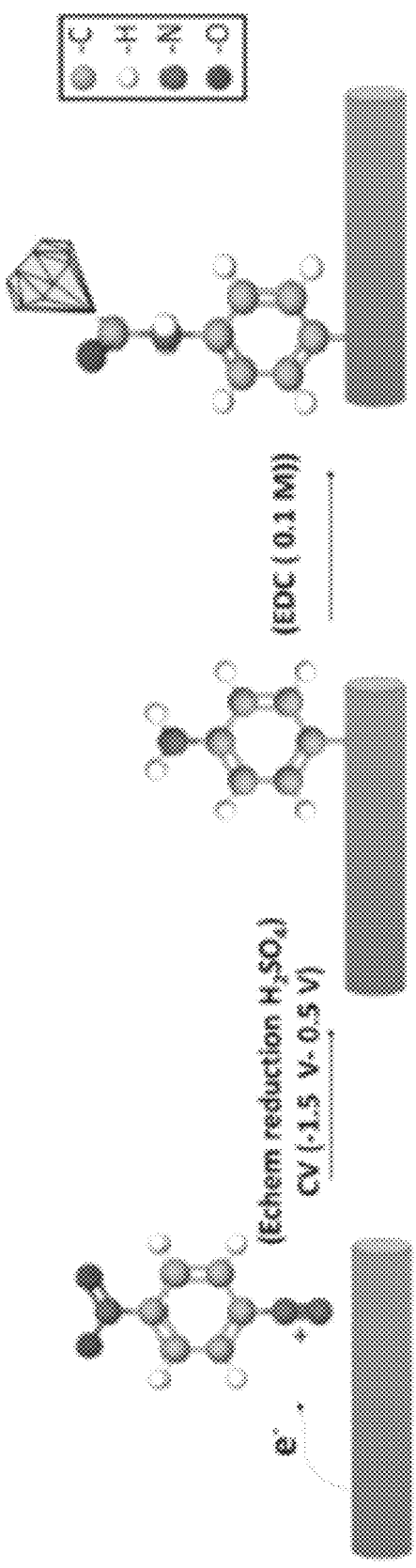
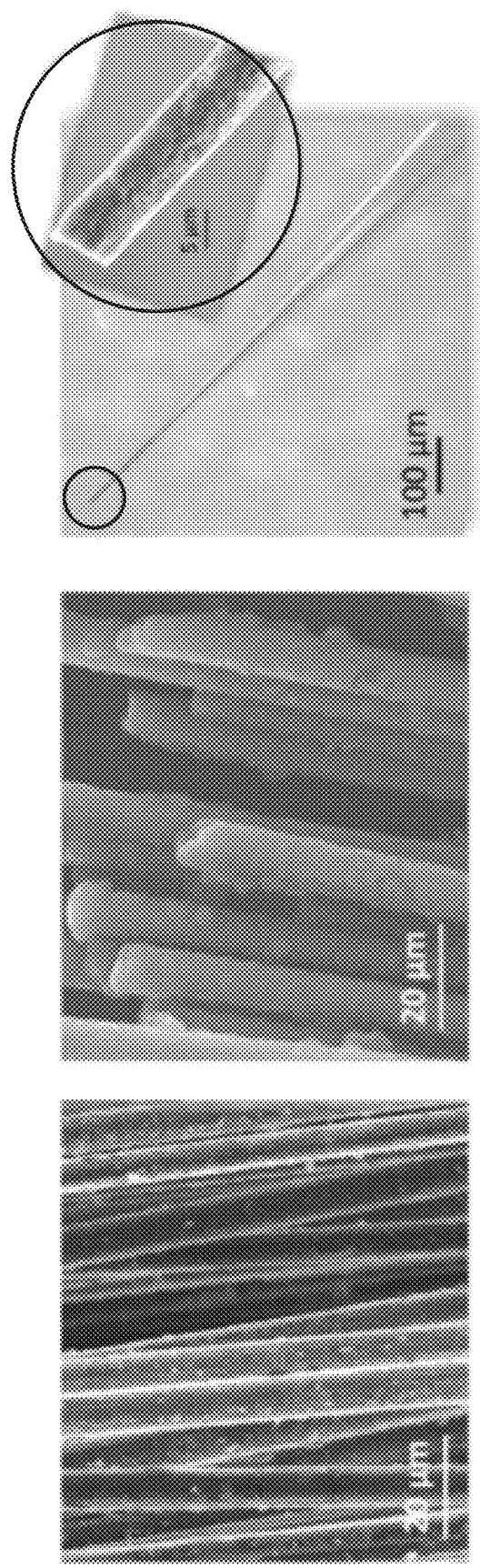
Figure 2a  Figure 2b  Figure 2c  Figure 2d  Figure 2e  Figure 2f

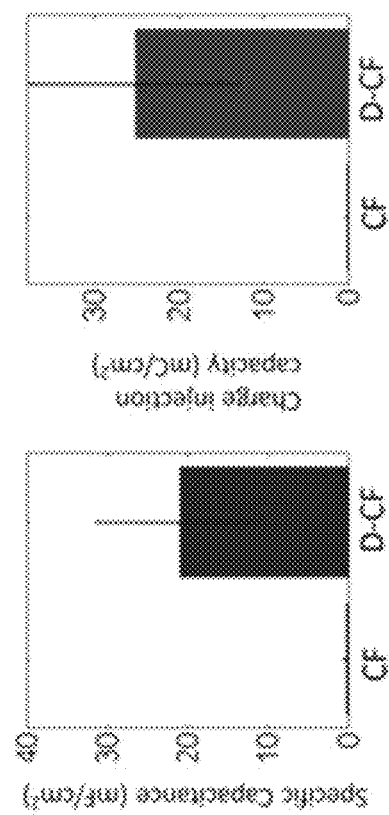
Figure 3d
Figure 3c
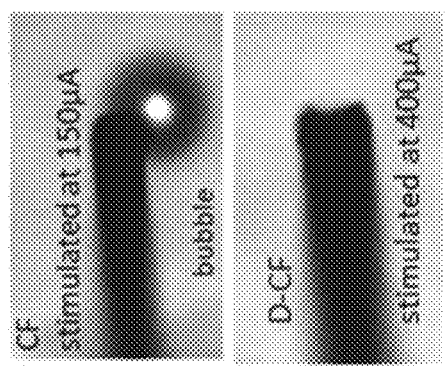
Figure 3b
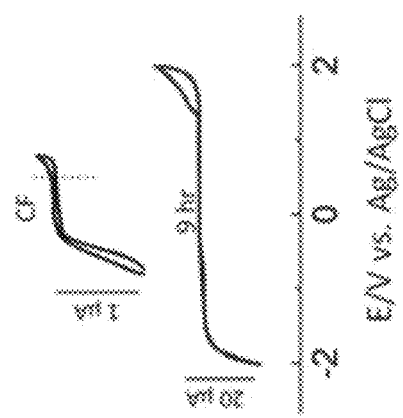
Figure 3a

METHOD OF FORMING A DIAMOND COATING ON A CARBON MATERIAL

CROSS-REFERENCE TO RELATED APPLICATIONS

This application is the U.S. National Phase under 35. U.S.C. § 371 of International Application PCT/AU2020/050114, filed Feb. 11, 2020, which claims priority to Australian Patent Application No. 2019900435, filed Feb. 11, 2019. The disclosures of the above-described applications are hereby incorporated by reference in their entirety.

TECHNICAL FIELD

This disclosure relates generally to the formation of a diamond coated substrate, such as a carbon-containing material. The disclosure relates particularly, though not exclusively, to the formation of a conductive diamond layer on a carbon substrate.

BACKGROUND

Electrodes can be used in an array formation for neural recording and stimulation or for electrochemical sensing. The biological environment of such electrodes means that they must have specific properties such as being biocompatible and operate at electrical conditions that record and stimulate neural activity.

Carbon fibre electrodes have shown to be excellent for recording neural activity. However, carbon fibre electrodes are unsuitable for stimulating neural tissue as the electrochemical capacitance is too low. To make carbon fibres suitable for stimulating, the carbon fibres need to be modified. Diamond is a suitable coating because it has high electrochemical capacitance. However, diamond coatings on carbon fibres have been attempted with limited success due to etching of the carbon fibres during diamond deposition.

It is to be understood that, if any prior art publication is referred to herein, such reference does not constitute an admission that the publication forms a part of the common general knowledge in the art, in Australia or any other country.

SUMMARY

A first aspect of the disclosure provides a method of forming a conductive diamond layer on a surface of a carbon fibre substrate that is used as a component of an electrode for neural stimulation or electrochemical sensing. For example, the electrode may be capable of electrically stimulating a neuron and chemically sensing an environment of the neuron. The method comprises:
(i) functionalising at least a portion of the surface with a functionalising agent to facilitate coating the surface with the conductive diamond layer; and
(ii) providing a diamond precursor and depositing the diamond precursor over the functionalising agent to form the conductive diamond layer.

The conductive diamond layer may help to increase a surface area of the substrate and thereby increase the electrochemical capacitance of the substrate. Further, the inventors have observed that intrinsic surface properties of the diamond material also contribute to increasing the electrochemical potential. The use of a diamond precursor may help to reduce etching of the carbon fibre substrate during the deposition of the conducting diamond coating.

Throughout this specification the term "carbon fibre" is used to refer to fibres formed from generally amorphous, polymorphic or polycrystalline carbonaceous fibrous materials. The carbon fibre may also include other forms of carbon, such as $C_{60}$, graphene and carbon nanotubes, but these other forms of carbon maybe disbursed through the carbonaceous material. The term "carbon fibre" can include fibres such as carbon nanotubes.

Throughout this specification the term "diamond seeds" is to be interpreted broadly to include a chemical moiety, a group of chemical moieties, a particle, or a group of particles capable of acting as a nucleation site for the growth of diamond by e.g. chemical vapour deposition excited such as by plasma or hot filament. For example, a diamond seed may include nano-diamonds. The diamond seeds may for example have a diameter ranging from about 5 nm to about 1000 nm, but typically about 20 to about 100 nm.

In an embodiment, the method comprises after step (i) and prior to step (ii) coating at least a portion of the surface with diamond seeds to form a diamond seed layer. The conductive diamond layer may be deposited on the diamond seed layer.

Functionalising the surface with a functionalising agent may comprise functionalising the surface with a chemical moiety that is capable of forming a covalent bond with the diamond seeds. In some embodiments, the diamond seeds are bound to the substrate with electrostatic or Van der Waal forces. A combination of electrostatic/Van der Waal forces and covalent bonds may be used to bond the diamond seeds to the substrate. In some embodiments, the surface is functionalised with an amine or carboxylate group. In these embodiments, the diamond seeds may be bound to the surface via an amide bond. The amide bond may be formed through the use a coupling agent. When an amide bond is used to bind the diamond seeds to the substrate, the diamond seeds may be oxygen-terminated. The term "oxygen-terminated" is to be broadly interpreted to include a chemical moiety that includes an oxygen group, such as a hydroxy, carbonyl, carboxyl, aldehyde, ether or epoxy group. It should be appreciated that the "oxygen-terminated" site also includes other chemical moieties such as hydrogen e.g. the "oxygen-terminated" group is the majority of non-hydrogen species. The substrate may comprise an amine. For example, the functionalising agent may include an aminophenyl species. The amino group may be formed by a reduction step after the surface is functionalised with the functionalising agent. In an embodiment, the functionalising agent includes a diazonium moiety. The step of functionalising the surface of the substrate may include applying a negative charge to the substrate to electro-catalytically convert and eliminate the diazonium moiety on the functionalising agent as nitrogen gas so that a radical is formed on the functionalising agent. The radical can then react to form a covalent bond between the functionalising agent and the surface of the substrate.

In an embodiment the method comprises, prior to coating at least a portion of the surface with diamond seeds to form a diamond seed layer, disbursing the diamond seeds in a solution to form a diamond seed solution. Coating at least a portion of the surface with diamond seeds to form a diamond seed may include immersing the surface in the diamond solution.

In an embodiment, the substrate is one of a plurality of substrates. In this embodiment, functionalising the surface with the functionalising agent may comprise functionalising one or more of the plurality of substrates. The one or more of the plurality of substrates may be specifically selected.

For example, the plurality of electrodes may be arranged in a grid, and an outside perimeter of the grid may be functionalised with the functionalising agent.

In an embodiment, step (ii) comprises providing a mixture of gas and then subjecting the diamond seed layer to microwave plasma-assisted chemical vapor deposition or hot filament chemical vapour deposition in the presence of the mixture of gas to form the conductive diamond layer. The conductive diamond layer will generally include a dopant. The dopant may be nitrogen-based or boron-based. The mixture of gas may include nitrogen, argon, methane, hydrogen and/or trimethyl boron. However, it should be appreciated that the mixture of gas may include any gas having one or more constituents that contain nitrogen, carbon and/or boron i.e. a mixture of gas that contain dopants. In some embodiments solid sources of nitrogen-, carbon- and/or boron-containing compounds are etched to generate in-situ gaseous molecules that contain nitrogen, carbon and/or boron. The mixture of the gas may be selected to form a nitrogen-doped or boron-doped conductive diamond. However, it should be appreciated that overall the diamond layer is conductive, but the diamond layer material is not completely diamond and the conductivity is not necessarily caused by the dopant.

In an embodiment, step (ii) further comprises coating a least a first portion of the surface with a mask to limit the formation of the conductive diamond layer at a second portion of the surface. The mask may be formed from a metal, such as molybdenum. The mask may be in the form of a stage. The second portion may include a tip of the fibre. For example, only a tip of the carbon fibre may be coated with the conductive diamond layer. Additionally, only a top of the carbon fibre may be coated with the diamond seed layer. The diamond seed layer may be uniform over the at least a portion of the surface. The method may further comprise the step of depositing an insulating layer, such as a non-conductive diamond layer, before and/or after step (ii). The method may further comprise encapsulating the electrode in an inert material such as glass, parylene, aluminium nitride (AlN), or alumina ($Al_2O_3$)

The disclosure also provides an electrode comprising a conductive diamond layer formed on a surface of a substrate using the method as set forth above.

The disclosure also provides an electrode for stimulating neural activity or to perform electrochemical sensing comprising: a conductive carbon fibre substrate; a base layer covalently bonded to at least a portion of the substrate; and a conductive diamond layer covering at least a portion of the substrate.

The base layer may be bonded to the substrate via an amide bond. An amine of the amide bond may be located on the base layer. The base layer may include an aminophenyl species. The base layer may be provided as nanodiamonds from which the conductive diamond layer is grown. The conductive diamond layer may be grown from the base layer via microwave plasma-assisted chemical vapor deposition. The nanodiamonds may have a diameter ranging up to about 100 nm. In some embodiments the base layer includes diamondoid structures such as adamantane. In an embodiment the nanodiamonds have a diameter ranging from about 30 nm to about 35 nm. The base layer may be uniform over the at least a portion of the surface.

When the electrode is in contact with neurons, a current required to be passed through the electrode to stimulate 100% of the neurons may have an average value of 70 μA. When the electrode is in contact with neurons, a current required to be passed through the electrode to stimulate 100% of the neurons may have an average value of 150 μA. The electrodes may have a length ranging from about 0.01 mm to about 10 mm, and a diameter greater than 2 μm. The conductive diamond may be N-doped or B-doped diamond. The conductive diamond layer may be located at a tip of the carbon fibre. The substrate may be one of a plurality of substrates. One or more of the plurality of substrates may comprise the conductive diamond layer. Put another way, only some of the substrates of the plurality of substrates may have the conductive diamond layer. In an embodiment, the electrode further comprises a non-conductive diamond layer positioned: over the seed layer, and/or over the conductive diamond layer.

The disclosure also relates to an electrical device for neural stimulation and/or performing electrochemical sensing comprising the electrode as set forth above.

The disclosure also relates use of the disclosed electrode to stimulate neurons and/or electrochemical sensing. In an embodiment, an environ of the neurons is chemically sensed using the same electrode as is used to electrically stimulate the neuron.

A substrate comprising the conductive diamond layer of an embodiment of the disclosure may be used in electrical applications, such as the use of a supercapacitor.

An embodiment of the disclosure may provide an electrode that is suitable for neuron stimulation and that has an electrochemical capacitance that is higher than an untreated (i.e. native) carbon fibre. An electrode of an embodiment of the disclosure may have the capabilities required for therapeutic intervention. An advantage of using a carbon fibre as the substrate may be that its conductivity and flexibility are maintained for an implantable material.

BRIEF DESCRIPTION OF FIGURES

Embodiments will now be described by way of example only with reference to the accompanying non-limiting Figures.

FIGS. 2a-2c shows: (a) electrochemical grafting of nitrophenyl diazonium to a carbon fibre (CF); (b) subsequent electrochemical reduction to an aminophenyl linker layer; and (c) covalent coupling of carboxylic acid functionalized nanodiamonds to form a chemical vapour deposition (CVD) seed layer.

FIGS. 2d-2f shows: SEM images of (d) seeded and (e) diamond-coated CFs; and (f) optical image of a single diamond-coated CF electrode encapsulated in a glass pipette with the SEM image of the electrode tip shown in (f) inset.

FIG. 3*a* shows cyclic voltammograms used for estimating the water-window for carbon fibre (CF) (0.4 V) and diamond coated carbon fibre (D-CF) electrodes FIG. 3*b* shows microscope images of CF and D-CF. The images show CF electrolyzing water and forming gas bubbles with 150 μA amplitude pulses compared to D-CF electrodes where no bubbles form even with 400 μA pulses. Pulse duration: 0.5 ms.

FIG. 3*c* shows specific capacitance increased from 0.263±0.168 mF/cm$^2$ on CF to 20.90±10.30 mF/cm$^2$ on D-CF electrodes.

FIG. 3*d* shows that the CIC of D-CF was 238 times larger than that of CF, which increased from 0.105±0.067 mC/cm$^2$ to 25.08±12.37 mC/cm$^2$.

DETAILED DESCRIPTION OF EMBODIMENTS

Figure 1:
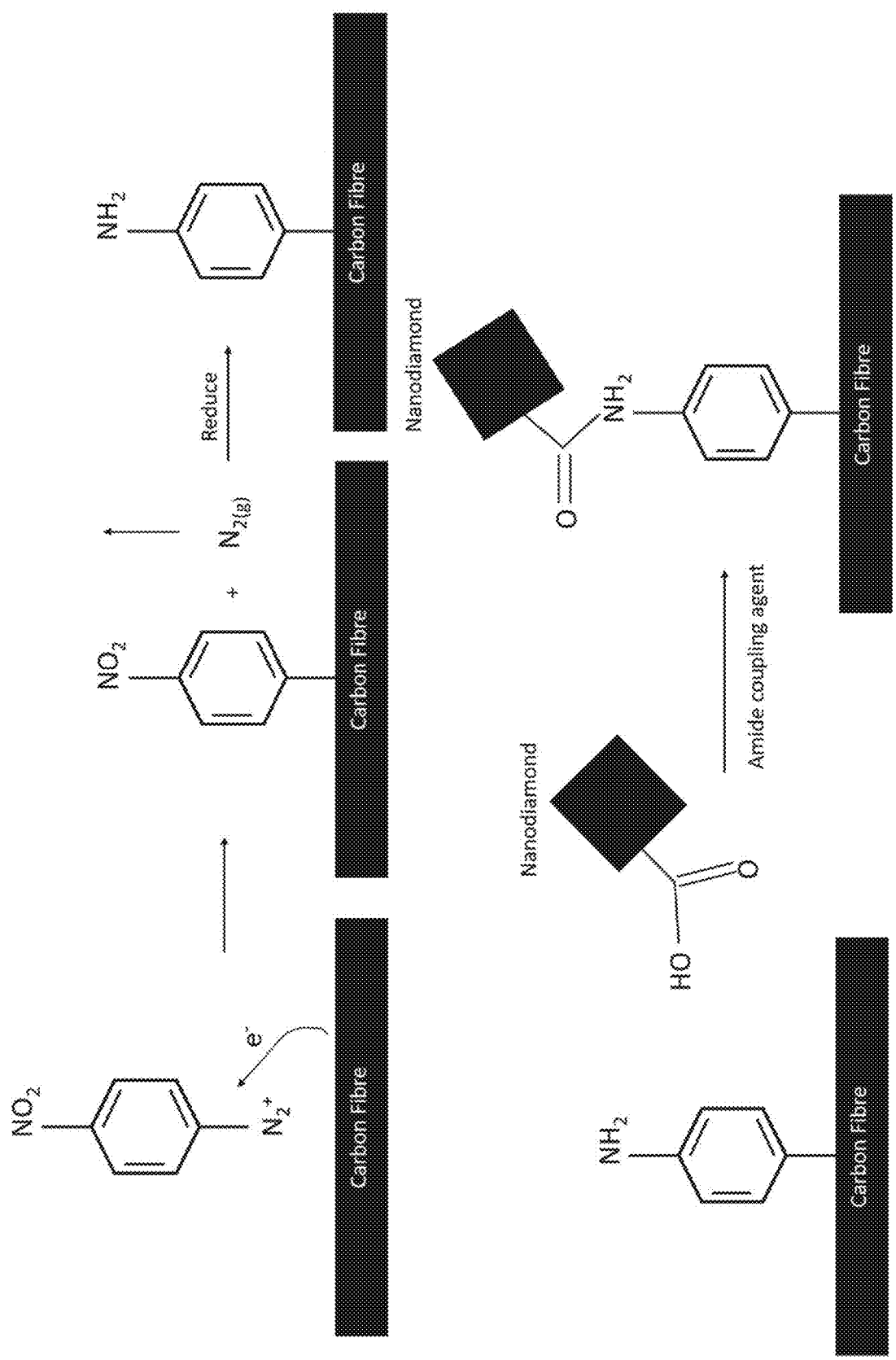
FIG. 1 shows a schematic reaction scheme for the forming a conductive diamond layer on a surface of a carbon fibre substrate.

An embodiment provides a method of forming a conductive diamond layer on a surface of a substrate, comprising:
(i) coating at least a portion of the surface with diamond seeds to form a diamond seed layer; and
(ii) providing a diamond precursor and depositing the diamond precursor on the diamond seed layer to form the conductive diamond layer.

The substrate may be conductive. When the substrate is conductive, the substrate may be part of an electrical device. For example, the substrate may form part of an electrode. The substrate may form part of a supercapacitor. The substrate may be planar. The substrate may be carbon-based. The substrate may be a fibre. In an embodiment the substrate is a carbon fibre. The fibre may have a diameter >0.5 μm. For example, the carbon fibre may have a diameter ranging from about 1 μm to about 200 μm. In some embodiments the fibre has a diameter greater than about 2 μm, such as 5 μm. In some embodiments, the diameter of the fibre ranges from about 5 μm to about 20 μm.

The diamond seeds are a moiety(ies) or a group(s) or compound(s) or particle(s) that are capable of seeding the growth of diamond in a later synthetic step e.g. in step (ii). For example, the diamond seed may be a monolayer applied to the substrate which promotes favourable diamond growth characteristics. The diamond seed layer may be uniform. The diamond seed layer may be in the form of a film. The diamond seeds can include compounds such as diamondoids. In an embodiment the diamond seeds are provided as diamonds. For example, the diamonds may be nanodiamonds. The nanodiamonds may have a diameter of <100 nm, such as <50 nm. In an embodiment the diameter of the nanodiamonds is >5 nm. The diameter of the nanodiamonds may be provided as a range.

For example, in an embodiment, the diameter of the nanodiamonds ranges from about 30 nm to about 35 nm. Having a small range of nanodiamond diameters may help to ensure that the diamond seed layer is substantially uniform in surface roughness. The nanodiamonds may be polycrystalline and/or monocrystalline. The crystallinity of the nanodiamonds may be irrelevant so long as they have enough diamond bonds to act as a nucleating site. The nucleation site may act as a nucleation layer for the subsequent growth of the conductive diamond layer.

A thickness of the diamond seed layer may be determined by the type of compound(s) used to form the diamond seed layer. Generally, the thickness of the diamond seed layer is determined by the dimensions of the moiety(ies) or a group(s) or compound(s) or particle(s) used to form the diamond seed layer. If the diamond seed layer is formed from nanodiamonds, the thickness of the diamond seed layer will generally be about the same as the diameter of the nanodiamonds. For example, if the nanodiamonds have a diameter ranging from about 30 nm to about 35 nm, the diamond seed layer will have a thickness of about 30 nm to about 35 nm. Having a uniform diamond seed thickness can help to ensure that the resulting conductive diamond layer is also uniform in thickness.

Step (i) of the method may comprise purifying the nanodiamonds prior to coating the substrate. Purification may be used to remove any nanodiamonds with a diameter outside a desired range. For example, the nanodiamonds may be disbursed into a solution and centrifuged to remove any nanodiamonds having a diameter greater than a desired size and/or to remove nanodiamond aggregates.

In some embodiments the diamond seeds are bound to the substrate with a functionalising agent. The functionalising agent may allow more favourable chemistries to attach the diamond seeds to the substrate such that any degradation to the substrate is minimised during conductive diamond layer formation. In an embodiment the functionalising agent includes a chemical moiety that is capable of forming a covalent bond with the diamond seeds. For example, the functionalising agent may include an amine, alcohol, carboxylic acid, aldehyde, ketone, nucleophile and/or leaving group such as a halide. The covalent bond may be formed using nucleophilic substitution, catalysis and/or coupling agents. For example, a covalent bond between the functionalising agent and the substrate may be formed by Heck, Stille, Suzuki and/or Sonogashira reactions. In an embodiment the functionalising agent includes an amine or a carboxylic acid, and the diamond seed includes the other of the amine or carboxylic acid. If the functionalising agent and diamond seed have either an amine or carboxylic acid, an amide bond can be formed between the functionalising agent and the diamond seed. The amide bond can be formed using a suitable coupling agent, including carboiimide-based coupling agents such as N,N,N',N'-tetramethyl-O-(1H-benzotriazol-1-yl)uronium hexafluorophosphate (HBTU), N-(3-Dimethylaminopropyl)-N'-ethylcarbodiimide hydrochloride (EDC·HCl), and N,N'-dicyclohexylcarbodiimide (DCC).

The functionalising agent may be bound to the substrate with electrostatic interactions and/or covalent bonds. For example, a functionalising agent may be firstly bound to the substrate due to electrostatic forces. The functionalising agent may then be covalently bonded to the substrate. When the diamond seeds are provided as a solution, coating the surface of the substrate with the diamond seeds can include immersing the substrate in the solution. For example, when nanodiamonds are used as the diamond seeds, they can be disbursed in an aqueous solution by assistance with sonication, such as ultrasonication, and aqueous coupling techniques can be used e.g. to form an amide bond using EDC·HCl.

In an embodiment the substrate is functionalised with an aminophenyl species. The amino group can be provided once the functionalising agent has been bonded to the substrate. For example, a functionalising precursor can be bound to the substrate and then converted to the functionalising agent having a corresponding moiety capable of forming a covalent bond with the diamond seed. The functionalising agent may have a protected amine, and the protecting group, such as Boc or Fmoc, may be removed once the functionalising agent is bonded to the substrate. In other examples, the functionalising agent may comprise an amine precursor, such as a nitro group, that can be converted to an amine, such as with reduction, once the functionalising agent is bonded to the substrate. In an embodiment, a 4-nitrobenzenediazonium salt can be covalently bonded to a carbon substrate using an electro-catalysed reaction by applying a negative potential to the substrate. Once the 4-nitrobenzenediazonium group has been bonded to the substrate, the nitro group can be reduced to the corresponding amine. In some embodiments, reduction of the nitro group and bonding through the diazomium moiety is performed in a single step. Electro-catalysed reactions to functionalise the substrate, for example using diazonium-containing compounds, may be preferred since these reaction conditions do not degrade the carbon fibre. Any subsequent steps to afford the functionalising agent may preferably use mild reaction conditions to ensure any degradation to the substrate is minimised.

The use of electro-catalysed reactions with diazonium-containing compounds means that a negative charge may be applied to specific electrodes to carry out functionalisation. Given that it is only the electrode(s) with the negative charge that are functionalised, when a plurality of substrates are used, a negative charge may be applied to only one or more of the substrates so that the substrates with the negative charge may be functionalised with the diazonium-containing species. Put another way, step (i) may selectively functionalise one or more of the plurality of substrates. This means that not all of the plurality of substrates requires functionalisation, and functionalisation may occur on specific electrode(s). This may be used to form specific electrode architectures. For example, when the plurality of substrates is in the form of a grid, specific rows and/or columns may be energised with a negative charge so that functionalisation only occurs on the energised substrates.

An embodiment of a reaction scheme to coat at least a portion of the surface with diamond seeds to form a diamond seed layer is shown in FIG. 1 and FIGS. 2a-2c. Note that the components and compounds depicted in FIGS. 2a-2c are not to scale and are illustrative only. Negative charge is applied to a carbon fibre which firstly attracts 4-nitrobenzenediazonium cation towards the surface of the carbon fibre due to electrostatic forces. At the same time, the negative charge applied to the carbon fibre results in electro-catalytic elimination of nitrogen gas and the formation of a covalent bond from the phenyl group at the 1 position to the carbon fibre. Although the Figures depict a 4-nitrobenzenediazonium salt, any of a 2-, 3- and/or 4-nitrobenzenediazonium salt can be used. It should be noted that an alkyldizaonium species could be used in place of an aryldiazonium species. In some embodiments the functionalisaing agent is not conjugated with the substrate. The nitro group is then reduced to the amine, such as with sodium borohydride or lithium borohydride. The amino moiety from the aniline group bonded to the carbon fibre is then coupled to the carboxylic acid on the nanodiamond using an amide coupling agent to form the corresponding amide.

The diamond precursor is a mixture capable of forming the conductive diamond layer. In an embodiment the diamond precursor is a mixture of gases that are reacted via microwave plasma-assisted chemical vapor deposition to form the conductive diamond layer from the diamond seed layer. The mixture of gas can include nitrogen, argon, methane, hydrogen and/or trimethyl boron. In an embodiment, the mixture of gas comprises nitrogen, argon and methane, for example 20% nitrogen, 79% argon and 1% methane that are deposited via microwave plasma-assisted chemical vapor deposition at a temperature of about 1000° C. In an embodiment, the mixture of gas comprises hydrogen, methane and trimethyl boron and are deposited via microwave plasma-assisted chemical vapor deposition at a temperature of about 850° C. In some embodiments hot filament chemical vapour deposition is used during step (ii) to form the conductive diamond layer. The specific gases in the mixture of gases can be used to form a specific type of conductive diamond. For example, when the mixture of gas includes nitrogen the resulting conductive diamond is N-doped, and when the mixture of gas includes a form of boron such as trimethyl boron the resulting conductive diamond is B-doped. In some embodiments changing a thickness of the conductive diamond layer affects the electrochemical properties of the resulting electrode. In some embodiments, the conductive diamond layer is positioned on top of the diamond seed layer i.e. the diamond seed layer and the conductive diamond layer are separate layers that contact one another at an interface therebetween.

A thickness of the conductive diamond layer is dependent on the reaction conditions used to form the conductive diamond layer. Generally, the longer a reaction time for chemical vapour deposition, the thicker the conductive diamond layer. For example, after 6 hours of growth the conductive diamond layer may have a thickness of about 2 µm, and after 22 hours of growth the conductive diamond layer may have a thickness of about 10 µm.

When the substrate is a fibre, the conductive diamond layer may be formed along a whole length of the fibre. For applications where the substrate is used as a component of an electrode that is used for neural stimulation, the conductive diamond layer is generally provided on an exterior surface of the electrode. Not all embodiments require the conductive diamond layer to be formed along a whole length of the substrate e.g. fibre. In these embodiments the conductive diamond layer can be provided on a portion of the substrate. For example, when the substrate is a fibre such as a carbon fibre, the conductive diamond layer may surround a portion of the carbon fibre that includes tip of the fibre. In this way, the conductive diamond layer may be provided towards a tip of the fibre.

When only a portion of the substrate is covered with the conductive diamond layer, the method may use a masking step to mask out any region of the substrate where the conductive diamond layer is not required. For example, the mask may cover a first portion of the carbon fibre, such as a base of the electrode, to limit the formation of the conductive diamond layer at a second region of the carbon fibre, such as at a tip of the carbon fibre. In some embodiments a stage is used to physically mask a region of the substrate, and thus the diamond seed layer, not requiring the conductive diamond layer. Such a stage may be provided by a molybdenum-based stage. In embodiments when a stage is used, the stage will cover a portion of the substrate prior to step (ii) of forming the conductive diamond layer. In some embodiments, the stage also covers a portion of the diamond seed layer. In some embodiments the masking step may be provided by a masking layer that is applied directly to the substrate. The masking step can be removed at a later step, for example by etching. In an embodiment, a masking layer may be applied directly to the substrate prior to the substrate being coated with the diamond seed layer. In this embodiment, the conductive diamond layer should only grow from a region of the substrate that is coated with the diamond seed layer. In another embodiment the substrate is coated with the diamond seed layer, and then a masking layer is provided prior to forming the conductive diamond layer at step (ii). In either embodiment, the masking layer can be removed in a final step. In some embodiments, the mask is applied to the substrate prior to step (i) to limit the formation of the diamond seed layer to an unmasked region of the substrate. The mask can then be moved and step (ii) performed. Alternatively, step (ii) can be performed then the mask can be removed.

In an embodiment, an insulating (i.e. non-conductive) layer/coating may be provided over the conductive diamond layer. The insulating layer may be a non-conductive diamond layer. The non-conductive diamond layer may be provided over a portion of the conductive diamond layer. For example, when the conductive diamond layer only covers a tip region of the carbon fibre substrate, the non-conductive diamond layer may only cover the tip region that is covered by the conductive diamond layer. However, in some embodiments, the non-conductive diamond layer may cover more than that a region of the carbon fibre covered by the conductive diamond. For example, if the conductive diamond layer covers 20% of the carbon fibre substrate, the non-conductive layer can cover more than 20% of the carbon fibre substrate. Put another way, a region covered by the non-conductive diamond layer is larger than a region covered by the conductive diamond layer. In some embodiments a region covered by the conductive diamond layer is larger than a region covered by the non-conductive diamond layer. In an embodiment, the insulating layer may be formed on top of the conducting diamond layer so as to isolate an end of the fibre so that only the end acts as a region for stimulation and/or recording.

During formation of the insulating layer, a mask may be used to mask a region of the electrode that does not require the non-conductive diamond layer. The insulating layer may be provided over an entirety of the electrode. In these embodiments a mask is not required during the formation of the non-conductive diamond layer. In some embodiments, a first region of the carbon fibre is covered by the conductive diamond layer and a second region of the carbon fibre is covered by the non-conductive diamond layer. For example, a tip of the carbon fibre may be covered by the conductive diamond layer and the remainder (e.g. shank) of the carbon fibre may be covered by the non-conductive layer.

Once the conductive diamond layer is formed on the carbon fibre substrate to form the electrode, the electrode may be encapsulated with an encapsulant. The encapsulant may be inert. The encapsulant may be glass. For example, the electrode may be encapsulated in a glass fibre. The encapsulant may be a non-conductive or insulative layer.

Figure 2G:
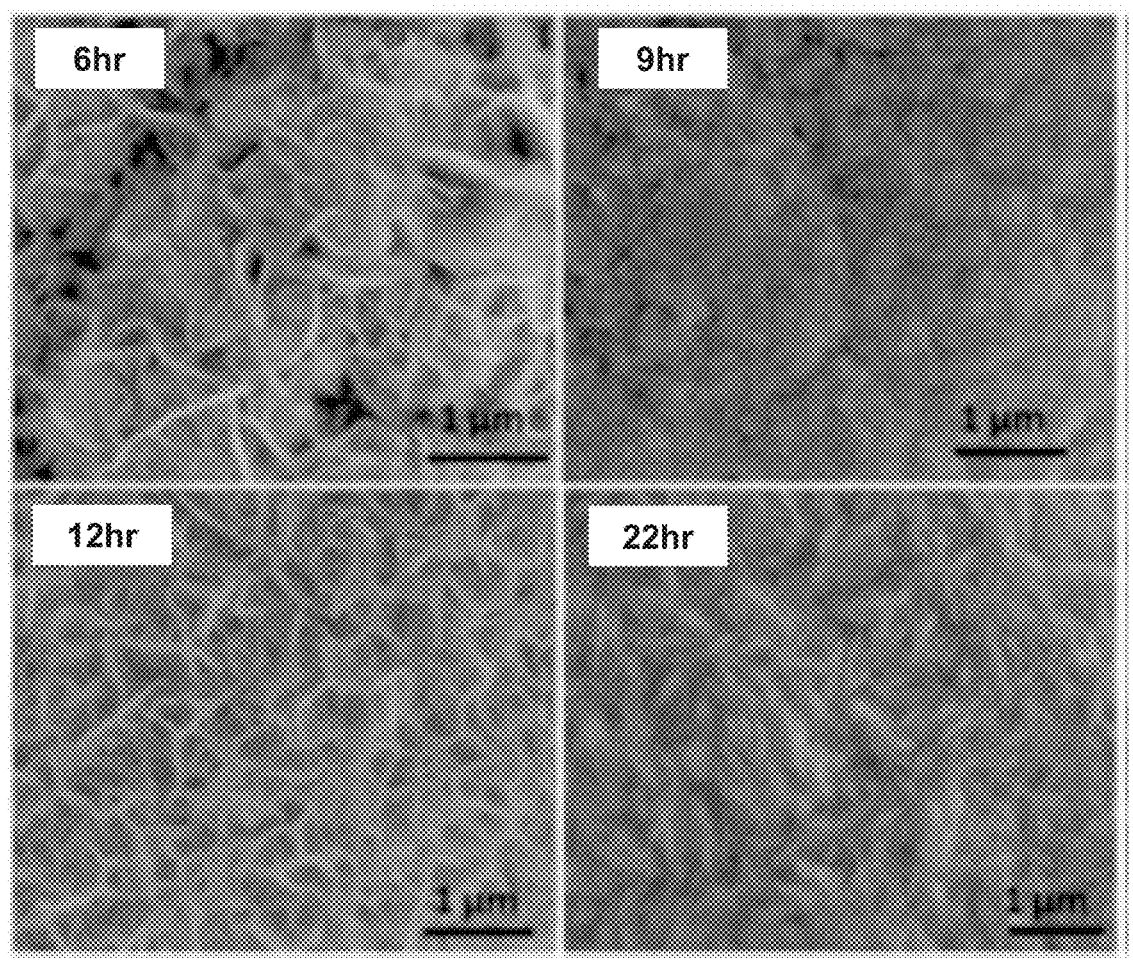
FIG. 2g shows high magnification scanning electron micrograph (SEM) images of nitrogen doped ultra-nanocrystalline conductive diamond (NUNCD) surface after deposition times between 6 and 22 h.
Figure 2H:
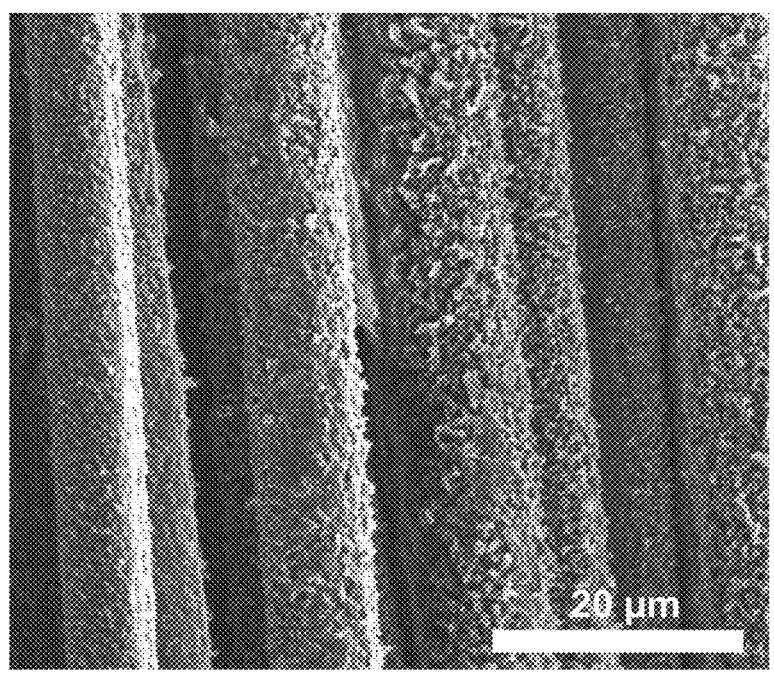
FIG. 2h shows a SEM of carbon fibres following growth of a boron doped layer of diamond.

FIG. 2h is a scanning electron microscope image of carbon fibres following growth of a boron doped layer of diamond. A thickness of the conductive diamond layer in FIG. 2h is greater than about 1 µm. The layer of diamonds on the carbon fibre substrate has a high degree of nanoscale and microscale roughness. This roughness results in a large increase in surface area and hence in electrochemical capacitance. Unlike other materials, because the layers covering a portion of the substrate are primarily made of diamond, it is unlikely that they will degrade within the body or under a wide range of alternative application conditions. In some embodiments the electrode may be used for electrochemical sensing, such as sensing specific analyte(s).

In an embodiment, a single electrode may record, stimulate and/or chemically sense. In an embodiment, an electrode can record, stimulate and chemically sense. Two or more of recording, stimulating and sensing modalities may occur at the same time from the same electrode. The diamond coating may not degrade the capacity of the electrode to record neural signals. The conductive diamond layer may help to transform the carbon fibre, which is known to be a good recording electrode, into a multimode electrode capable of the recording, stimulation and chemical sense functions. In comparison, prior art single electrodes are unable to record and stimulate and chemically sense from the same electrode.

EXAMPLES

Non-limiting Examples will now be described.
Methods
Modification of Carbon Fibres Before nanodiamond seeding, polyacrylonitrile (PAN) PAN-based carbon fibres (CFs) (Goodfellow) were electrochemically functionalized with aminophenyl groups on the surface. The electrochemistry was performed in a Teflon cell with a three electrode set-up using a Gamry Potentiostat (Interface 1000E). An Ag/AgCl electrode and a Pt wire were used as the reference and counter electrode, respectively. A cluster of CFs was connected to a copper wire via silver epoxy. The CFs were first subjected to an acetonitrile solution containing 0.1 M tetrabutylammonium tetrafluoroborate (Sigma) and 1 mM 4-nitrophenyl diazonium tetrafluoroborate (Sigma). Five potential cycles between 0.2 V and −0.6 V vs Ag/AgCl was performed at a scan rate of 200 mV/s. The nitrophenyl modified surfaces were sequentially rinsed with acetonitrile, acetone, and deionized water, then exposed to a 0.1 M $H_2SO_4$ solution. The nitrophenyl groups were electrochemically reduced to aminophenyl groups by five potential cycles between 0.5 V and −1.5 V vs Ag/AgCl at a scan rate of 200 mV/s. The modified CFs were again rinsed with acetonitrile, acetone and deionized water, and trimmed off from the copper wire to remove silver epoxy for further use.

Forming Diamond Seed Layer

Modified carbon fibres were seeded with oxygen terminated nanodiamonds either via electrostatic attraction or covalent binding. Commercially available nanodiamond powder was first annealed in oxygen at 400° C. for 5 h, and then prepared as solution with deionized water at a concentration of 1.5 mg/ml. The solution was subsequently ultrasonicated for 1.5 hours and centrifuged for 12 hours to remove large nanodiamond particles and aggregates. According to ZetaSizer measurement, the final nanodiamond showed concentration of $1.21*10^8$ particles/ml with zeta potential at −30 mV and an average particle size of 30-35 nm. To form electrostatic attraction, aminophenyl terminated carbon fibres were ultrasonicated with oxygen terminated nanodiamond solution for 5 minutes, and then rinsed with deionised water and dried in air. The covalent binding was formed by immersing the treated carbon fibres in nanodiamond solution containing 0.1M N-(3-Dimethylaminopropyl)-N'-ethylcarbodiimide hydrochloride (EDC·HCl) at room temperature overnight. The carbon fibres were then rinsed with deionised water and dried in air.

Forming Conductive Diamond Layer

After nanodiamond seeding, the seeded carbon fibres were placed in a microwave plasma-assisted chemical vapor deposition system for nitrogen-included ultrananodiamond deposition. The fibres were masked with a molybdenum stage to limit the growth of diamond to the tips of the fibres. To form a N-doped conducting diamond layer, a gas mixture of 20% nitrogen, 79% argon and 1% methane was used, at a temperature at 1000° C., for deposition time varying between 6 and 22 hours. To form a B-doped conducting diamond layer, a gas mixture of 87% hydrogen, 4% methane and 9% trimethyl boron at a pressure of 40 torr and at a temperature of 850° C. is used.

Forming Microelectrodes

Single diamond-coated CFs were attached to copper wires by silver epoxy, encapsulated in glass capillaries and pulled to form microelectrodes with a micropipette puller (Model P-2000, Sutter Instrument Co). The length of the fibre exposed was adjusted to 100±10 μm under an optical microscope. The diamond-coated electrodes were then electrochemically oxidized three times by performing cyclic voltammetry in PBS from 0 to 2 V at a scan rate of 100 mV/s.

Surface Characterization

The nanodiamond solution was characterized with a Zeta-Sizer (Dynamic Light Scattering technique using a Zetasizer Nano ZS from Malvern). The morphology of the fibres before and after diamond deposition was obtained with SEM/FIB Nova 200 Nanolab, FEG Dual Beam (HV 5 KV, Current 6.3 nA, mode SE). K-edge NEXAFS measurements were conducted at the Soft X-Ray beamline of the Australian Synchrotron. All measurements were conducted in the total electron yield mode, recorded using sample drain current to collect a signal of all secondary electrons and thus data from the bulk of the samples. Double normalization was conducted with an 'IO' gold grid partially inserted into the beam, to monitor fluctuations in beam intensity for all scans, and normalized to a reference photodiode scan for beamline transmission function (primarily for removal of beamline carbon-based absorption characteristics). Raman spectra were performed on fibres using Renishaw RM 1000 Raman Stellar Pro 514 Modulaser (514 nm excitation source) with 100 mW power at room temperature. XPS (Thermo- Fisher K-Alpha) was used to obtain the chemical composition of the diamond fibres using an Al Ka radiation source at a power of 300 W and a spot size of 400 μm. High-resolution scans were performed using the flood gun function to compensate for charging at a step size of 0.1 eV and pass energy 50 eV. For electrochemical characterization, CV and electrical impedance spectroscopy (EIS) measurements were performed using a potentiostat (Gamry, Interface 1000E). All voltammograms were obtained with the electrodes immersed within a Teflon electrochemical cell of three electrodes, where platinum and Ag/AgCl are counter and reference electrodes, respectively. All experiments were conducted in 1 M PBS (0.13 M NaCl) at room temperature without nitrogen gas bubbling. Electrical impedance spectroscopy (EIS) was performed for estimating the specific capacitance of the electrodes. The recording was then fit with a Reap2Cpe circuit. Charge Injection Capacity (CIC) was also estimated from voltage transients during a constant current stimulation pulse according to the method of Annu. Rev. Biomed. Eng. 10 (2008) 275-309.

In Vitro Retinal Ganglion Cell Stimulation

Calcium imaging data came from retinas extracted from Long-Evans rats older than 3 months, of either gender. All experimental procedures conformed to the policies of The National Health and Medical Research Council of Australia (NHMRC) and were approved by the Animal Experimental Ethics Committee of the University of Melbourne (Ethics Approval #: 1814462). Animals were initially anesthetized with a mixture of ketamine and xylazine prior to enucleation. After enucleation, the rats were sacrificed with an overdose of Letharbarb (intracardiac). To load retinal ganglion cells with calcium indicators, 0.5 µl of 20 mM OGB-1 (hexapotassium salt dissolved in DI water) was injected into each eye through the optic nerve. The cornea and lens were removed, and the retina was left inside a dish with carbogenated Ames medium overnight at room temperature. The retinas were then cut into three pieces, mounted onto a glass slide with ganglion cell layer up, and held in place with a perfusion chamber and stainless-steel harp fitted with Lycra threads (Warner Instruments). Once mounted in the chamber, the retina was perfused (4-6 ml/min) with heated carbogenated Ames medium (33-35° C.). D-CF electrodes were then placed 200 µm above the inner limiting layer. All procedures were conducted under dim light conditions.

Calcium transients of retinal ganglion cells in response to electrical stimulation were then recorded with an upright confocal microscope (Olympus, FV 1000). The images were obtained with an excitation laser at 473 nm through a Nikon Plan Apo 0.75-numerical aperture (NA) ×20 objective. Stimuli were delivered using a Ripple system and images were acquired at 7 Hz and synchronized to the onset of each stimulus. Each stimulus was composed of ten groups of biphasic pulse trains (60 Hz, 0.5 ms phase duration, cathodic first), with each train composed of ten pulses. Stimuli were delivered ten times at 2 s intervals and repeated over ten monotonically increasing amplitudes. The percentage of electrically evoked calcium transients was then fit with a sigmoidal curve and the threshold was defined as the stimulation amplitude that yielded a 50% response. Data processing was performed in Fiji (ImageJwin64) and Matlab R2014a.

In Vitro Retina Ganglion Cell Recording

The recording capabilities of diamond-coated electrodes were also tested in vitro with a retinal whole mount preparation, similar to that stated in the stimulation session above. No calcium indicator was injected, and the retina was mounted with retinal ganglion cell side up immediately after dissection. Extracellular recordings were obtained by placing the electrode tip in contact with the retinal surfaces. A large platinum ground electrode was position in the perfusion solution at least 2 cm away from the retinal fragment. Signals were amplified, filtered with a hardware bandpass filter (5 Hz-15 Khz), sampled at 50 Khz and digitized (Tucker Davis Technologies: RZ2 base station and PZ2 multichannel recorder). The hardware high pass filter was set as low as possible to capture Local Field Potentials (LFPs), while rejecting large transients which could saturate the amplifiers. The low pass filter was kept as high as practical. This raw signal is shown throughout the disclosure without any additional post-processing. Light responses were obtained using a ~100 µm light spots centered at the electrode. The ratio of spikes, 1 s prior and 1 s after light stimulation, were compared. Additionally, the instantaneous changes in responses from 1 s prior compared to 1 s after a change in illumination were also analysed. Spikes were detected when the recorded signal crossed a threshold of eight standard deviations computed from the entire recording. A spike cluster analysis was used to classify and group spike waveforms with similar shapes. Once clustered, the SNR was calculated to evaluate the quality of the recordings. The signal quality was defined according to the SNR, which was calculated as the peak-to-peak amplitude of the mean waveform of the cluster divided by twice the standard deviation of the noise:

$$SNR = (S\text{-pp})/2\sigma\text{Noise}$$

where S-pp is the mean peak-to-peak amplitude of the spike amplitude, and alloise is the standard deviation after all the identified spike waveforms had been removed.

In Vivo Visual Cortex Recording

Surgery and Preparation

In vivo experiments involved recording using diamond coated electrodes from the primary visual cortex of a Tammar Wallaby (Macropus Eugenii), which is a species that has had its cortex studied extensively using traditional tungsten-in-glass electrodes. Before surgery, the animal was given lincomycin (10 mg/kg) and spectinomycin (20 mg/kg) intramuscularly and paraffin oil (10 ml) orally to reduce intestinal bloating during prolonged anesthesia. Anesthesia is induced with intramuscular injection of ketamine (10 mg/kg), medetomidine (0.015 mg/kg) and methadone (0.4 mg/kg). During surgery, the animal was given phytomenadione (Koagulon, 10 mg/kg) and tranexamic acid (Vasolamin, 100 mg/kg) intramuscularly in case of bleeding.

The animal was intubated then connected to a ventilator and anesthesiamachine. Inhalation of gaseous isoflurane (1-2% during surgery) and halothane (0.5% during recordings) with a 2:1 mix of O2 and N2O maintained anesthesia throughout the surgery and experiment. The animal's health was monitored throughout the entire experiment by checking the electrocardiogram (ECG), electroencephalogram (EEG), respiration rate, blood pressure, end-tidal CO2 concentration, and oxygen concentration. The animal's body temperature was monitored and maintained by a feedback-controlled heating blanket. Following surgery, the animal was paralyzed with vecuronium bromide (Vecuronium sun; 0.05 mg/kg for induction followed by a constant intravenous infusion at 0.1 mg/kg/h in Hartmann's solution containing 5% glucose) to prevent eye movements. The intravenous infusion of fluid was delivered through a tail vein at 2.5 ml/kg/h. Daily intramuscular injections were given to the animal: Atropine (0.05 mg/kg) to reduce salivation, dexamethasone (1.5 mg/kg) to prevent cerebral edema and a broad-spectrum antibiotic (Clavulox, 0.5 mL/kg) to control infection.

The head of the wallaby was stabilized with a stereotaxic frame and custom-made ear bars. A craniotomy was conducted from 3 mm to 20 mm posterior to bregma and approximately 2 mm-14 mm lateral from the midline to access the primary visual cortex (V1) in the left hemisphere. Then a durotomy was performed to expose the brain. A stainless-steel chamber was affixed to the skull with dental cement to stabilize the cortex during recording and prevent cortical tissues from drying out. To maintain moisture on the brain, 4% agarose in saline was frequently applied to the surface of the brain. Atropine sulfate eye drops (1%) were used to dilate the pupils and prevent accommodation. The corneas were protected with zero-power gaseous permeable contact lenses. At the termination of experiments, animals were euthanized by intravenous injection of an overdose of pentobarbitone sodium (Lethabarb; 150 mg/kg).

Visual Stimuli

Visual stimuli were generated with a ViSaGe visual stimulus generator (Cambridge Research Systems, Cambridge, UK) and displayed on a calibrated LED monitor (ASUS VG248 resolution 1920×1080 pixels). The LED monitor was viewed monocularly from 30 cm distance. A custom Matlab™ program was used to generate all visual stimuli (The Mathworks Inc. Natick, MA, USA). During single-unit recording, drifting sinusoidal gratings were presented to determine the preferred orientation of the recorded neurons.

Single-Unit Recording

Multi-unit activity (MUA) was recorded from the primary visual cortex. Recorded signals were amplified and filtered by the computer running the stimulation and recording software. Offline software from KiloSort was used to sort single units from MUA. After spike-sorting, single units could be readily identified. The responses of these units were then correlated with the stimulus presentation.

Simultaneous Detection of Dopamine and Uric Acid

CV studies were carried out to study the electrochemical response for different concentrations of dopamine (DA) and uric acid (UA) on electrochemically oxidized diamond carbon fibre electrodes with potentials scanned between –0.2 V and 0.8 V with respect to an Ag/AgCl electrode. Electrochemical oxidization of the electrode was performed in 3 mM of K4[Fe(CN)6] in 1 M KCl solution from 0 V to 2 V with 100 repetitive cycles and scan rated 1 Vs-1. It is noted that the limitation of detection (LOD) is determined using the following formula: LOD=mean blank+3σblank.

Results

Diamond Deposition on Carbon Fibre

Diamond coatings on CF have been attempted but with limited success. The difficulty is mainly associated with the etching of CF under the CVD environment necessary for diamond deposition. In order to protect the CF during CVD, an embodiment provides a method for pre-seeding CF with covalently bound nanodiamonds before diamond growth (FIGS. 2a and b). Covalent bonding of nanodiamonds was achieved by tethering nanodiamonds to the CF surface via a grafted aryl amine linker layer subsequently coupled to carboxylic acid terminated nanodiamonds via an amide bond (FIG. 2c) and described in more detail in the supplementary methods section. Successful covalent attachment of the aryldiazonium layer was confirmed by observation of the cyclic voltammogram (CV) during electrochemical deposition and subsequent reduction of the nitro group. X-Ray Photoelectron Spectroscopy (XPS) analysis confirmed both the presence of an aminophenyl film on the CF layer and the presence of amine groups following covalent coupling of carboxylic acid functionalized nanodiamonds.

Nitrogen-included ultrananocrystalline diamond (NUNCD) growth was performed on the covalently bonded surfaces for various growth times. With the sample grown for 6 h, carbon nanowalls (CNW) featured strongly in the resultant films. High-resolution SEM images (FIG. 2g) reveal that the surface is covered by ribbon structured CNW aligned perpendicular to the CF surfaces, with ultrananocrystaline diamond (UNCD) structures seen between the ribbons. After 9 h, NUNCD appears to have covered the surface of the CNWs. During this stage, the hydrogen atoms from the gas mixture in the CVD may react with sp or $sp^2$ carbon sites on the surface of the CNW and convert them into spa bonded carbon (diamond). At 12 h, re-nucleation and regrowth of CNWs on the NUNCD surface is observed. The results indicate that after 12 h, the condition is more suitable for nucleating and growing CNWs rather than nanodiamond and the nanosheet grows much faster in the direction parallel to the sheet due to the very high surface mobility of incoming C atoms or CHx radicals, and polarization of the graphitic layers. After 22 h deposition, a large number of CNW rendered a needle-like morphology (FIG. 2g). The growth of diamond on the substrate is shown schematically in FIG. 2j.

NEXAFS (FIG. 2i) is sensitive to the bonding structure $sp^2/sp^3$ and thus determines the type of carbon in a given area. The peak located around 285 eV corresponds to the transition C 1s→π* for the $sp^2$ C═C bond. At the surface of pure diamond due to surface reconstruction. The $sp^2$ peak intensity increased from the lowest to the highest attributed to the CF-NUNCD for 9 hr, 6 h, 12 h, and 22 h, respectively. The peak located around 289 eV is associated with core-level excitons in diamond material and the start of the conduction band edge. For pure diamond, the σ* (C]C) resonance should dominate, and the ratio of the intensities gives a figure of merit for the level from $sp^2$ to $sp^3$ bonding.

The edge feature at 292 eV is associated with a σ*(C═C) resonance, indicating graphitic materials. Conversely, an edge at 289 eV relates to σ* transitions at the onset of the conduction band edge. The remainder of the σ* region above 289 eV can be difficult to interpret, except for the presence of a clear second absolute band gap dip at ~302 eV which is unequivocally from the diamond. Thus, it can be seen that the 9 h sample shows a clear mixture of crystalline diamond and graphitic bonding. The 6 h sample shows a lower proportion of diamond-related features at 289 eV and 302 eV, while the other two samples show no clear evidence of diamond-like character. The relative intensity of the π* feature for all four samples scales inversely with the diamond-associated σ* features, confirming this analysis.

Figure 2I:
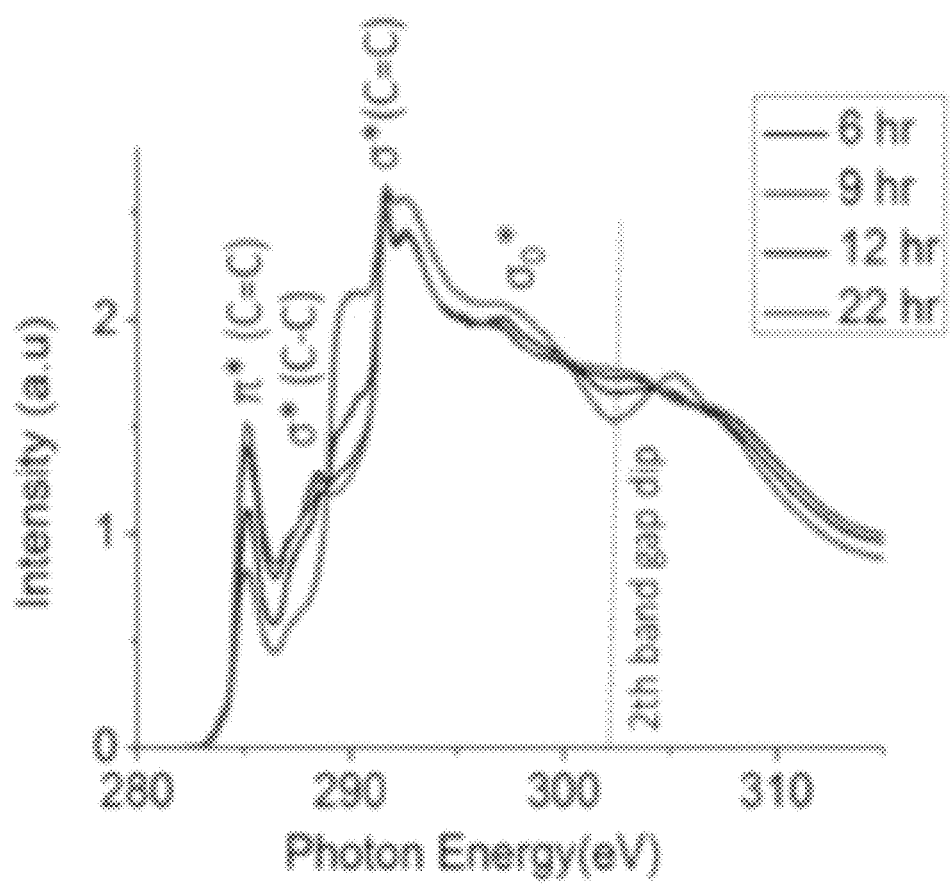
FIG. 2i shows near edge X-ray absorption fine edge structure (NEXAFS) spectrum from each surface is shown in FIGS. 2g at 6, 9, 10 and 22 hours.
Figure 2J:
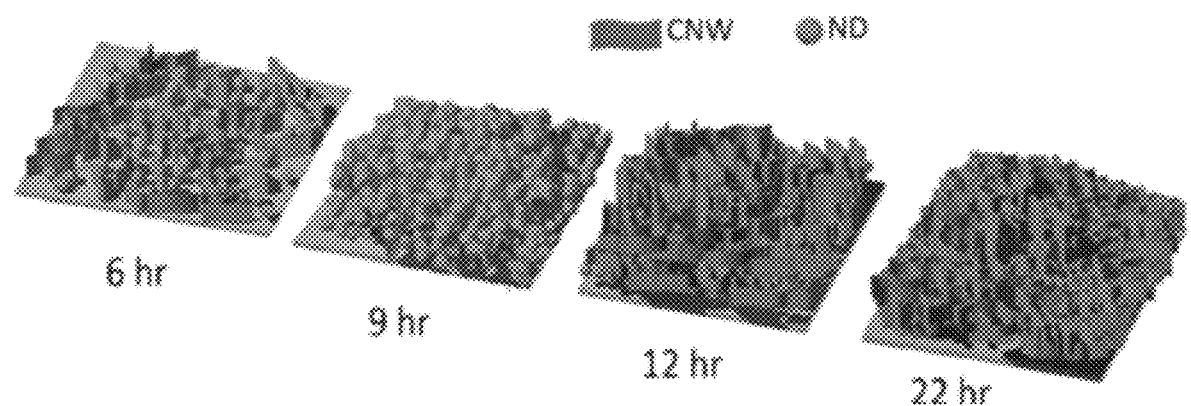
FIG. 2j shows a schematic representation of the change in surface structures from each surface shown in FIGS. 2g at 6, 9, 12 and 22 hours.
Figure 2K:
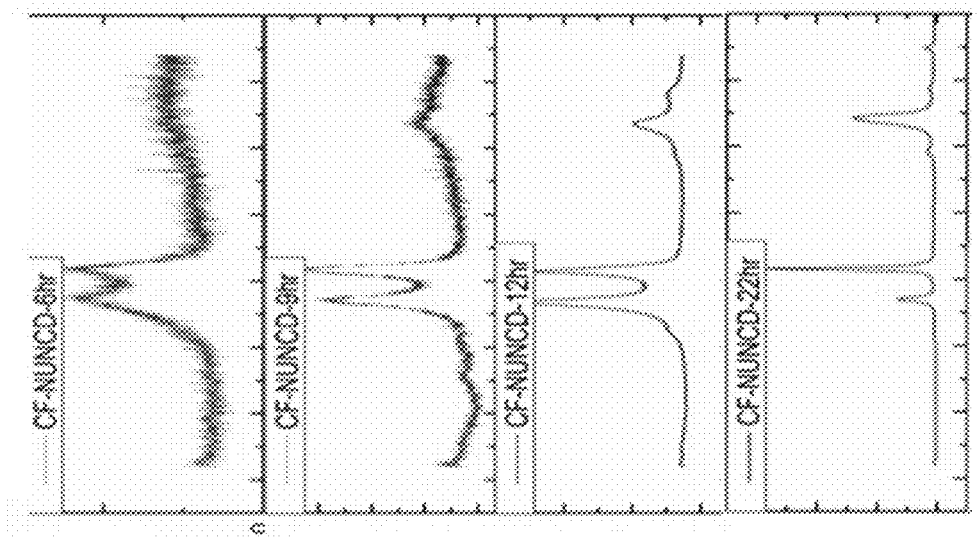
FIG. 2k show are Raman spectra of diamond coatings grown in accordance with embodiments of the present invention, illustrating growth of the diamond coating.
Figure 2L:
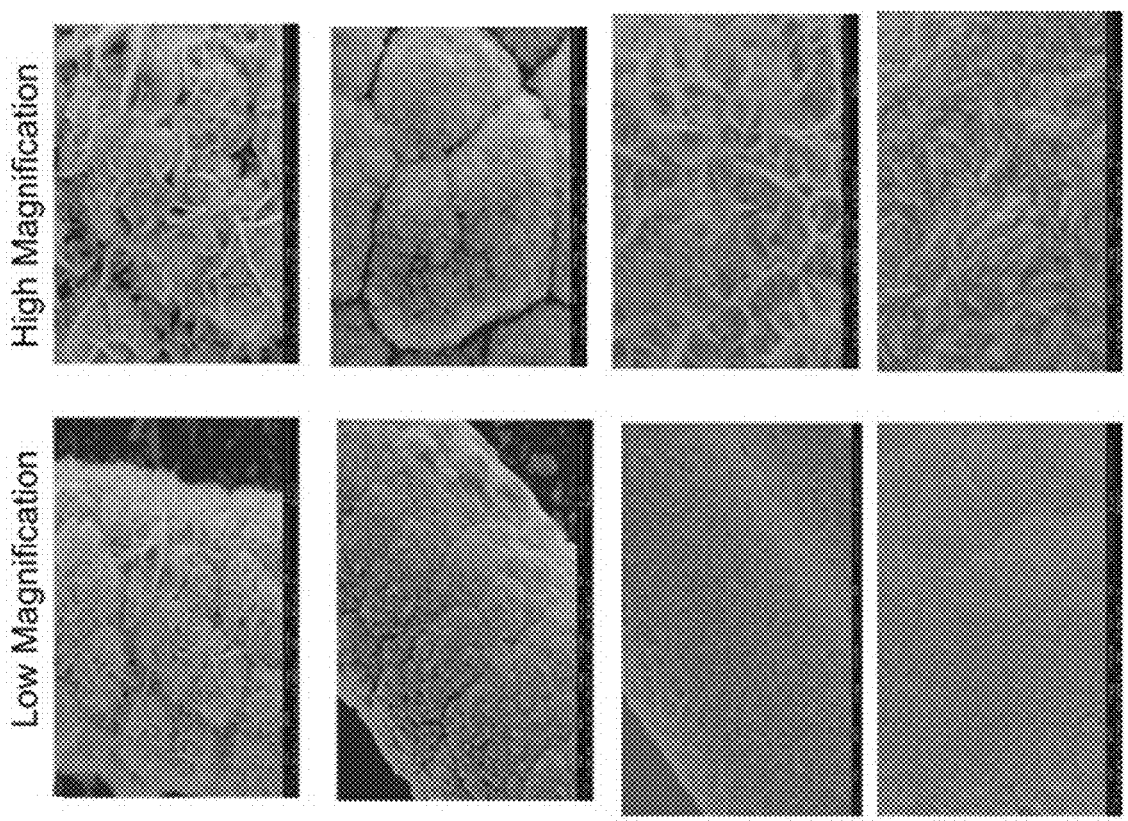
FIG. 2*l* show SEM micrographs of diamond coatings grown in accordance with embodiments of the present invention.

FIG. 2I is a scanning electron microscopy (SEM) micrograph taking at two different magnifications and for different growth period (growth period increasing from top to bottom, from 6 to 9, 12 and 22 hours), which illustrates the morphological changes of the diamond coatings with growth time. FIG. 2j are corresponding Raman spectra during formation of an embodiment of the disclosed electrodes.

Figure 2M:
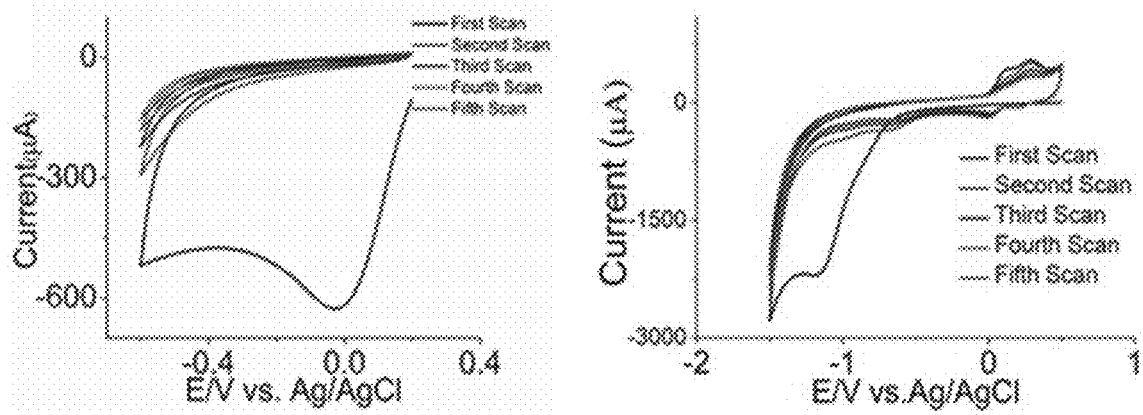
FIG. 2*m* show cyclic voltammetry graphs illustrating the successful two-step reduction of nitrophenyl and aminophenyl functionalized group onto the surface of a carbon fibre substrate.
Figure 2N:
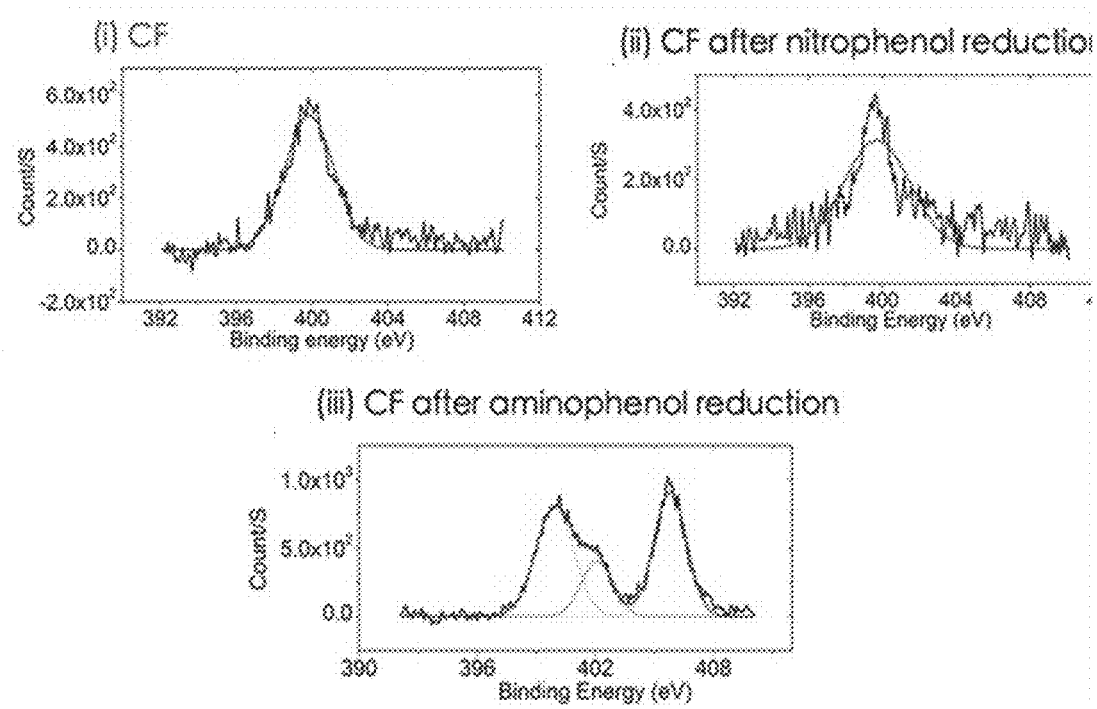
FIG. 2*n* shows XPS illustrating the successful two-step reduction of nitrophenyl and aminophenyl functionalized group onto the surface of a carbon fibre substrate.
Figure 2O:
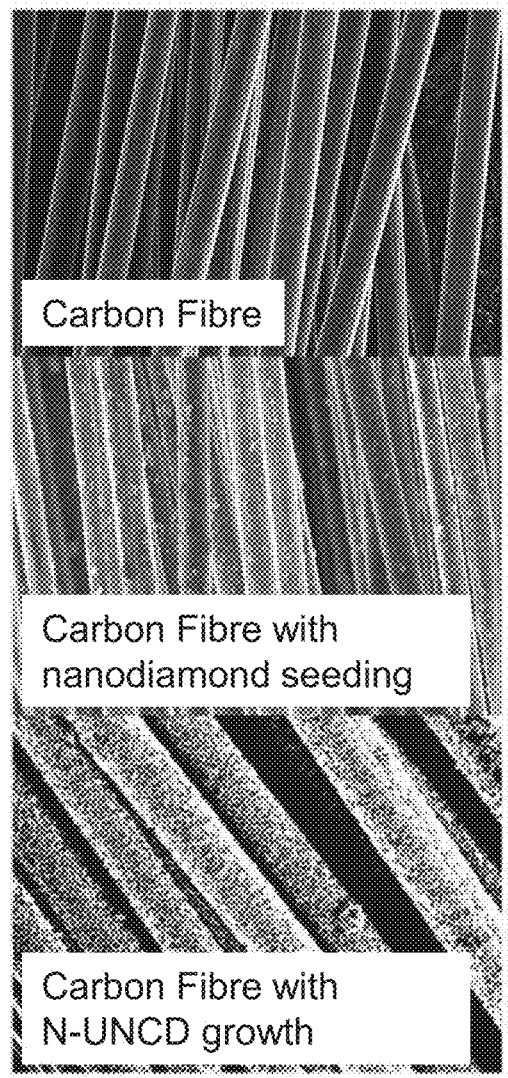
FIG. 2*o* shows SEM micrographs showing both the nanodiamonds seeding and nitrogen-doped conductive diamond layer coating grown in accordance with embodiments of the present invention.

FIG. 2m shows cyclic voltammetry graphs illustrating the successful two-step reduction of nitrophenyl and aminophenyl functionalized group onto the surface of a carbon fibre substrate. FIG. 2n shows high resolution Nis X-ray photoelectron spectroscopy (XPS) spectra including de-convolution illustrating the successful two-step reduction of nitrophenyl and aminophenyl functionalized group onto the surface of a carbon fibre substrate. FIG. 2o are scanning electron microscopy (SEM) images showing that both the nanodiamonds seeding and nitrogen-doped conductive diamond layer coating are uniform across the carbon fibre substrate.

Figure 2P:
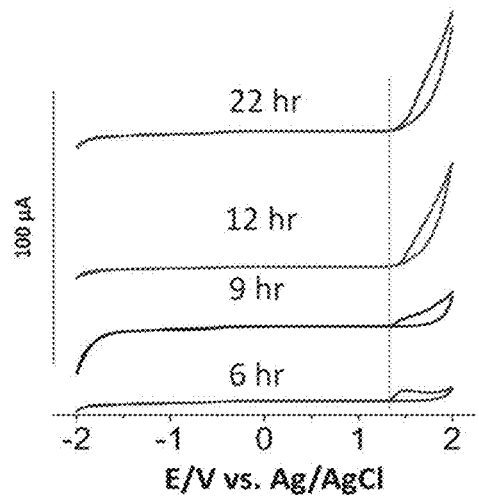
FIG. 2*p* shows cyclic voltammograms for carbon fibre after different growth time of nitrogen doped ultra-nanocrystalline conductive diamond (NUNCD).
Figure 2Q:
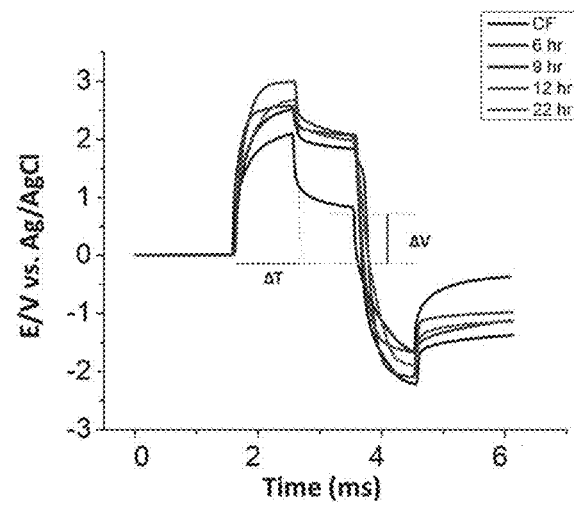
FIG. 2*q* shows voltage excursion measurements during 100 μA square wave current pulses with 1 ms in duration.
Figure 2R:
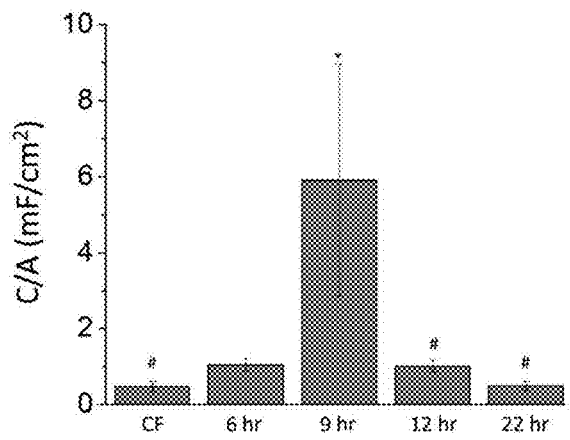
FIGS. 2*r* and 2*s* are plots showing capacitance and charge injection for carbon fibre with different times of NUNCD growth.
Figure 2S:
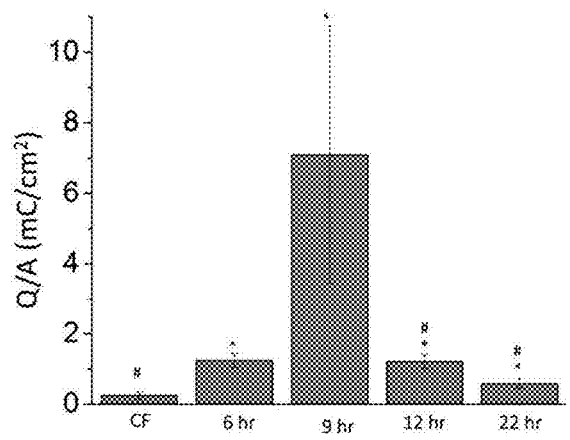

FIG. 2p is a cyclic voltammogram (CV) for carbon fibre after different growth time of nitrogen doped ultra-nanocrystalline conductive diamond (NUNCD). The scan rate was 100 mV/s. Reference and counter electrodes are Ag/AgCl and platinum, respectively. The CVs show that the voltage range of the water window increased after diamond growth compared to carbon fibre. i.e. became more diamond like. FIG. 2q is a voltage excursion measurement during 100 μA square wave with current pulses of 1 ms in duration. This was used to calculate the specific capacitance; FIG. 2r and FIG. 2s are plots showing capacitance and charge injection measurements for carbon fibre with different times of NUNCD growth.

Improved Charge Injection Capacity for Neural Stimulation

To be used for neural stimulation, single fibre electrodes were fabricated by first attaching the fibres onto a copper wire via silver epoxy and insulated inside a pulled glass capillary such that a 100±10 μm length of fibre was exposed to the solution.

Charge Injection Capacity (CIC)

CIC is a figure of merit used in neural stimulation research to describe the maximum amount of charge that can be injected during a single stimulation pulse before unsafe voltages occur on the electrode (i.e. before the water-window is exceeded). In this work, CIC was calculated using capacitance and water-window according to the following formula $$CIC = \frac{C_{dl} \times V_m}{GSA} \quad \text{(Equation (1))}$$

where $C_{dl}$ is specific electrochemical capacitance, $V_m$ is the voltage threshold to electrolysis of water and GSA is the geometric surface area of the electrode exposed to the solution. Here $V_m$ was estimated from cyclic voltammograms in PBS (FIG. 3a) and set at 0.4 V for CF and 1.2 V for all diamond-coated samples. $V_m$ is typically specified as a value that lies well within the water window limits, consistent with best practice for designing implants. $C_{dl}$ was measured by electrochemical impedance spectroscopy (EIS), fitted to an equivalent circuit model. The CIC for diamond-coated CF after different deposition times were measured to determine the optimal surface for neural stimulation. The GSA of the exposed fibres was estimated using SEM imaging, modelling the electrode as a smooth cylinder, and not taking surface roughness into account. Typically, electrodes were 10 μm in diameter and 100 μm in length yielding a GSA of 3200 μm².

Among electrodes, the specific capacitance was largest on coated CF with 9 hr NUNCD deposition (D-CF), when most of the surface was covered by spa bonded carbon. The specific capacitance increased approximately eighty fold from 0.263±0.168 mF/cm² on CF to 20.90±10.30 mF/cm² on D-CF (P<0.05, unpaired student t-test, FIG. 3c). As CF has significantly smaller water-window than diamond-coated samples, CIC of D-CF was 238 times larger than that of CF, increasing from 0.105±0.067 mC/cm² to 25.08±12.37 mC/cm² (FIG. 3d) (EIS fitting). Because of the size of the electrode used in this example, voltage transient plots were curved the onset of the voltage excursion were difficult to identify. By fitting a tangent to the curved voltage plots were able to estimate a Cal and CIC of 7.09±3.65 mC/cm², respectively.

FIG. 3b shows light microscope images of D-CF and CF electrodes during stimulation and illustrates the difference between the CIC for the two materials. For bare CF, water splitting, and gas bubble formation occurred at 150 μA during a 0.5 ms square wave current pulse (FIG. 3a). In contrast, the D-CF electrodes exhibit no bubble formation at 400 μA pulse amplitude (FIG. 3b).

Neural Stimulation with D-CF

The capability of embodiment of the disclosed electrodes to stimulate neurons was tested using live, wholemount explanted rat retina. A calcium indicator (Oregon Green 488 BAPTA-1) was loaded into Long-Evans rat retina via optic nerve injection and overnight diffusion. The retinas were kept perfused and alive during loading and during the subsequent experiment. The successful loading of calcium indicator cells was confirmed via confocal microscopy, as shown in FIG. 3e. The image shows effective staining of retinal ganglion cell somas, axon bundles, and blood vessels. Test electrodes were then placed 200 μm above the inner limiting membrane (top surface of retina), which mimics the condition when retinal prosthetics are implanted in patients when there is a gap between the electrodes and retinal surface due to limitations of the surgical implantation technique.

Figure 3F:
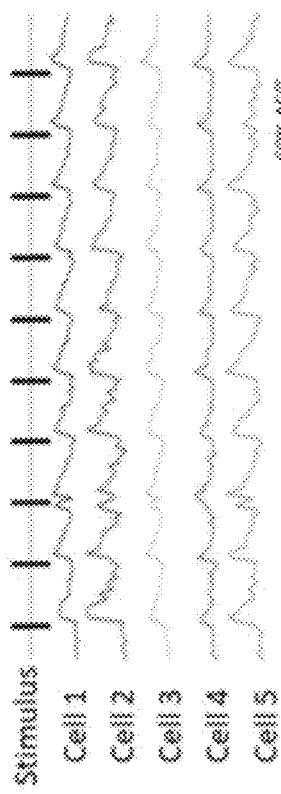
FIG. 3*f* shows calcium transients of cells 1-5 depicted in FIG. 3*e*.
Figure 5:
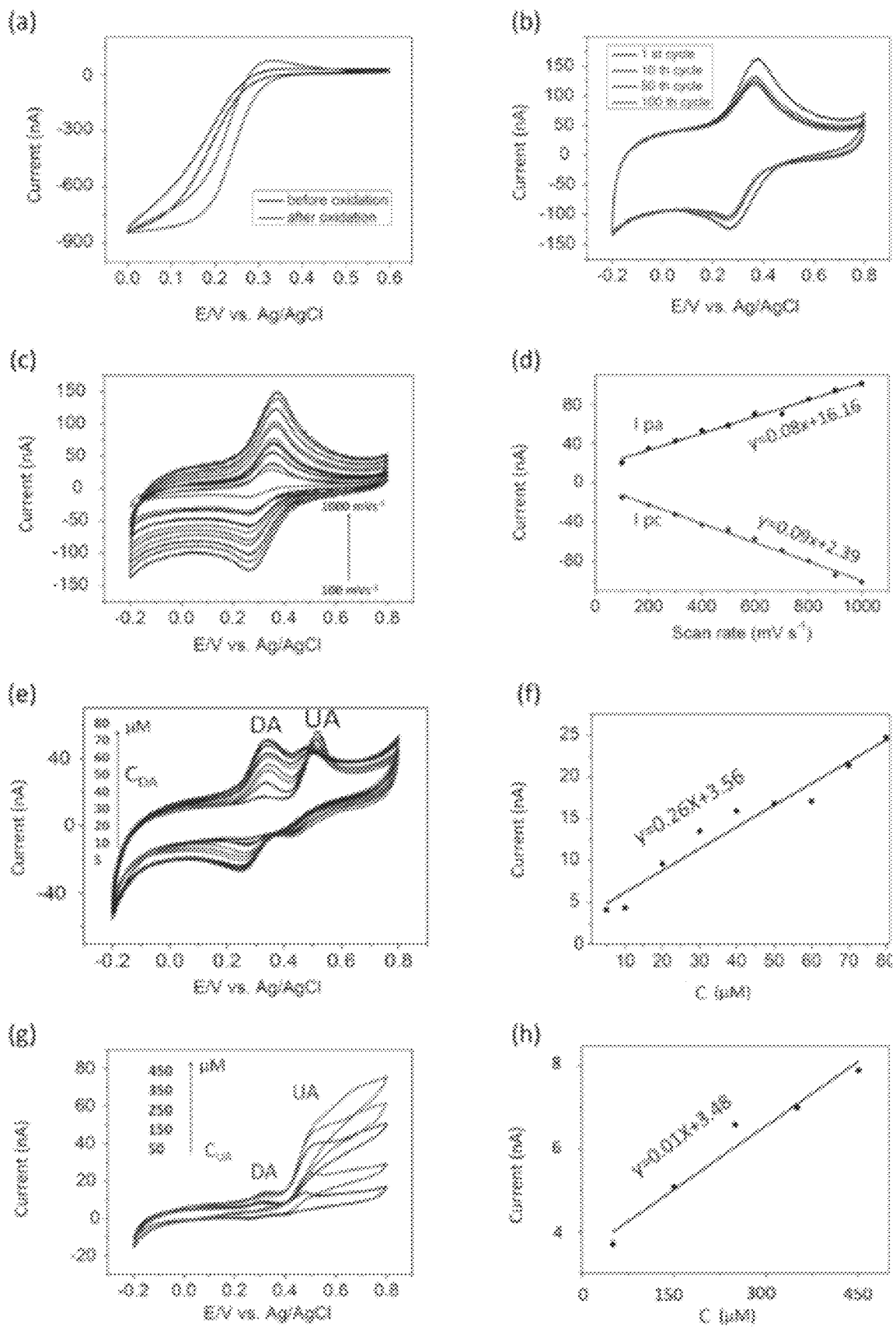
FIG. 5 shows simultaneous detection of dopamine and uric acid using cyclic voltammetry; (a) Cyclic voltammograms of 3 mM $K_3[Fe(CN)_6]$ in 1 M KCl using D-CF before and after electrochemical oxidization of the surface, scan rate 100 mVs$^{-1}$; (b) repetitive cyclic voltammetry response for 0.1 mM DA in 1×PBS for 100 cycles, scan rate 1 Vs$^{-1}$; (c) Cyclic voltammetric response on D-CF in 0.1 mM DA in a PBS at different scan rates and (d) their corresponding oxidation and reduction peak calibration plots; (e) Cyclic voltammetric curves of 100 μM UA in the presence of different concentrations of DA; (f) with their corresponding oxidation peak calibration plot, (g) cyclic voltammetric curves of 10 μM DA in the presence of different concentrations of UA, (h) with corresponding calibration curves (scan rate 100 mVs$^{-1}$).

FIG. 3f shows recorded calcium transients from the five example cell somas indicated in FIG. 5e during a stimulus train, composed of ten groups of pulses, each group starting at times indicated by the black bars in the line labelled "Stimulus". Each group of pulses is made up of ten cathodic first biphasic pulses with the same current amplitudes, 0.5 ms phase duration and 0.05 ms interphase gap at a frequency of 60 Hz. An effective stimulus causes an influx of calcium indicator into the soma and hence an increase in fluorescent intensity. Electrically evoked responses were detected by high pass filtering the fluorescence intensity of each RGC. Filtering was performed by convolving the signals with a difference filter [2 1 −1 −2]. The rapid changes in fluorescence was determined by thresholding at 1.5× the RMS noise level and then temporally correlating with the stimuli.

Figure 3G:
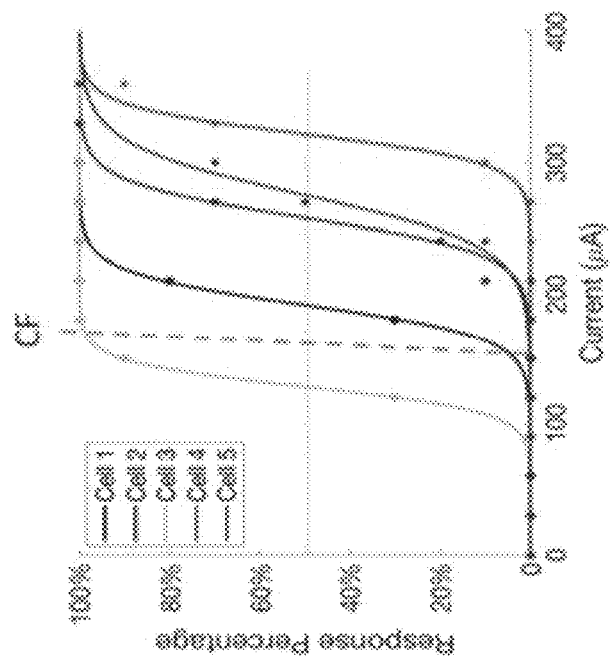
FIG. 3*g* shows sigmoidal curves that were fitted to the response rate for each neuron of cells 1-5 depicted in FIG. 3*e*. The neurons current threshold was defined as the current required to elicit a 50% response. The dashed red line indicates that current amplitude where water splitting occurred for CF.
Figure 3E:
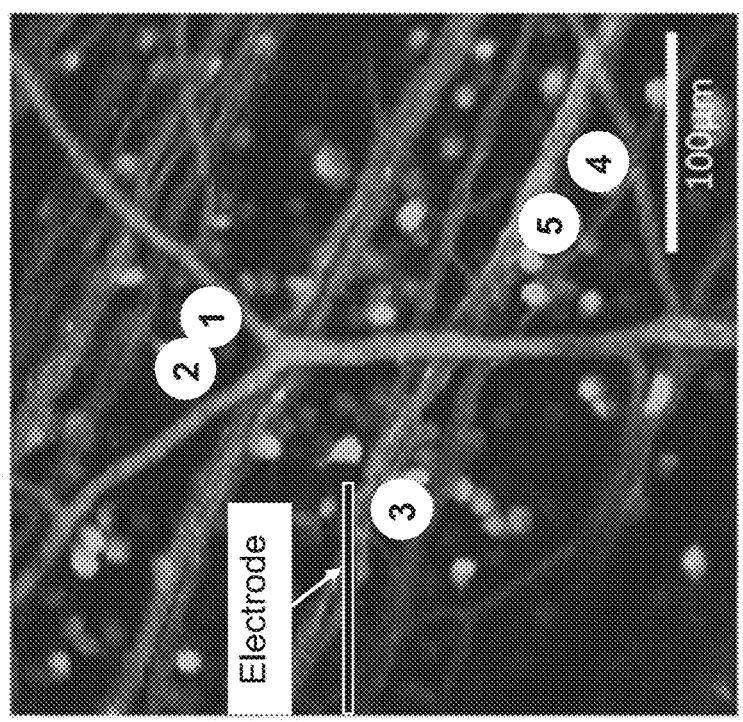
FIG. 3*e* shows fluorescence images that were collected in real time during electrical stimulation.

FIG. 3g shows the response curves for the example ganglion cells, which indicate the percentage likelihood of successful stimulation at various stimulation pulse current amplitudes. A stimulation efficacy of 100% was achieved at 150 μA for the most responsive neuron (cell 3) and approximately 380 μA for the least responsive neuron (cell 4). Uncoated CFs are not capable of safely delivering more than 150 μA (dashed line labelled "CF") and would therefore only be able to safely stimulate the most sensitive neuron measured. It is notable that stimulation threshold does not necessarily depend on distance from the stimulating electrode. This arises from natural variations between ganglion cells of the same type and the fact that many different ganglion cell types exist.

The threshold for stimulation of each neuron was defined as the current required to achieve 50% of the maximum (saturated) response and was estimated by fitting a sigmoidal curve to the response percentage of the cells under different stimulation amplitudes. The measurements were recorded using three electrodes on three pieces of retina, yielding an average stimulation threshold of 255.98±59.38 μA (51 activated neurons), 261.93±50.03 μA (40 activated neurons) and 292.55±79.89 μA (46 activated neurons), respectively. It is likely that different thresholds would be measured for different pulse durations and conditions.

High-Quality Single-Unit Neural Recording

Figure 4A:
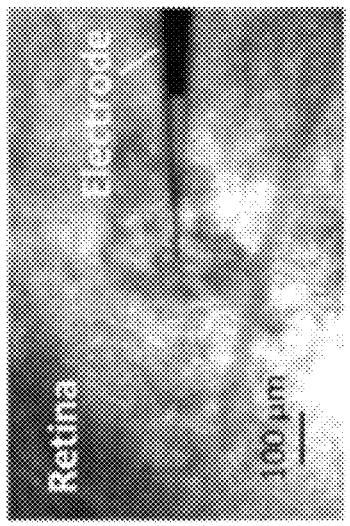
FIG. 4*a* shows D-CF electrodes placed in contact with the surface of excised retina.
Figure 4B:
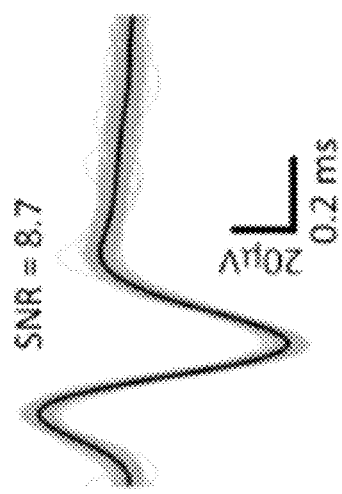
FIG. 4*b* shows individual spike waveforms from a representative recorded cell (grey traces) and the average spike waveform (black trace) for a single response trial. The average spike amplitude for this trial was 61.76±1.58 pV and had a signal-to-noise ratio (SNR) of 8.7.
Figure 4C:
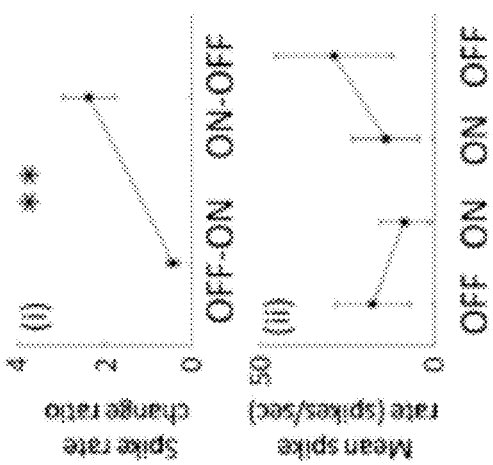
FIG. 4*c* shows (i) a change in firing rate of the recorded cell during the transition from light off-to-on and light on-to-off across four trials (a ratio greater than one corresponds to an increase in firing rate and less than one corresponds to a decrease) and (ii) the instantaneous firing rate during the transitions from light off-to-on and from off-to-on. Error bar represents standard deviation. **$p<0.01$ (Student t-test).
Figure 4D:
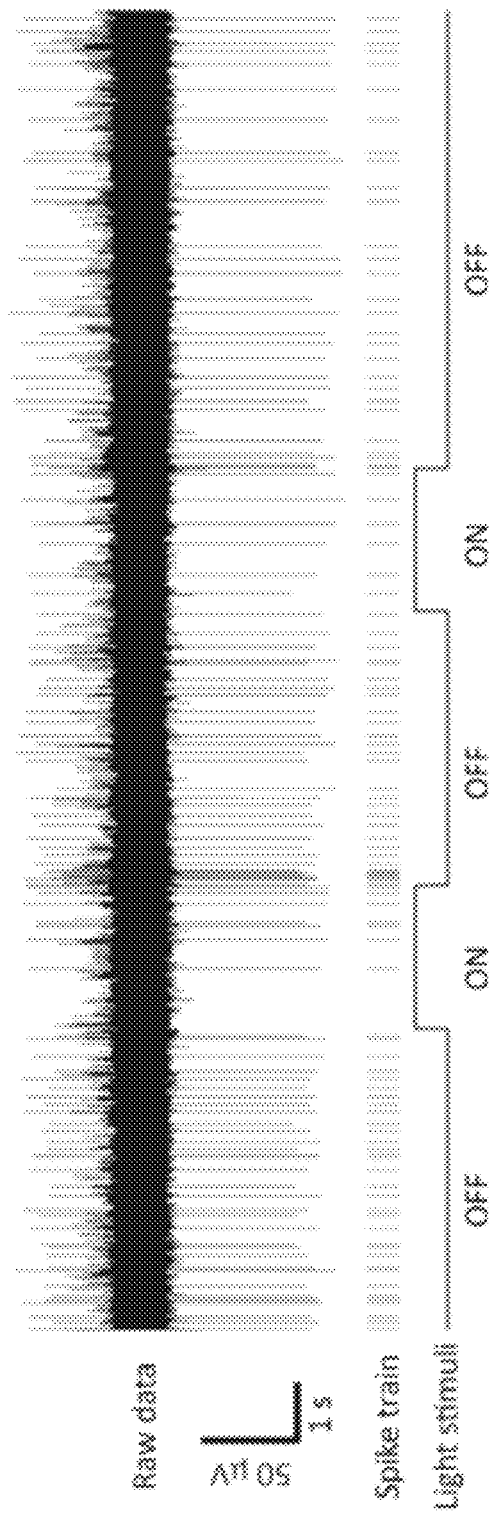
FIG. 4*d* shows a representative trial showing neural response to light stimulation.

The recording capability of D-CF electrodes was evaluated with explanted rat retinas in vitro (FIG. 4a-d), and separately in wallaby visual cortex in vivo (FIG. 4e-h). When testing with explanted retinas in vitro, the cell responded with an increase in firing rate when the light was turned off and a decrease in firing rate when the light was turned on (FIG. 4b-d). FIG. 4a shows the electrode placed into contact with the retinal surface. FIG. 4b shows the individual spike waveforms for a recorded cell (grey traces) and the average spike waveform (black trace). Spike-sorting was conducted using wave cluster and only one neuron was identified. The mean spike amplitude for this recording was approximately 61.76 ±1.58 μV The RMS noise from D-CF electrodes was approximately 19.0±1.8 μV in the extracellular solution, significantly lower than equivalent CF electrodes (50 μV). An improvement over time was observed in the recording quality of the electrode. The SNR for the trial shown in FIG. 4b was 8.7. The mean SNR across three light response trials was 6.36±2.37, which is comparable to previously reported values using a 15×15 μm NUNCD electrode (SNR: 7.25). The performance of the D-CF electrodes was also similar to previously reported recordings in cat cortex with a commercial tungsten electrode. FIG. 4c shows that the firing frequency of the recorded cell was significantly higher when the light was off compared to on indicating this was an OFF-ganglion cell. OFF-ganglion cells reduced their firing rate in response to light. The recorded response for one trial and the spike train relative to the light stimulus are shown in FIG. 4d. We repeated the experiment with three electrodes, all of which were able to record neural spikes.

To establish the efficacy of D-CF electrodes for high-resolution cortical recording, an experiment was conducted with the electrodes inserted into the visual cortex of an Australian marsupial (Tammar Wallaby, Macropus Eugenii) as part of ongoing comparative investigations. Wallaby has been shown to have a primary visual cortex (V1) with very similar anatomical and physiological properties to other mammals with high-resolution vision, such as primates and cats.

Figure 4E:
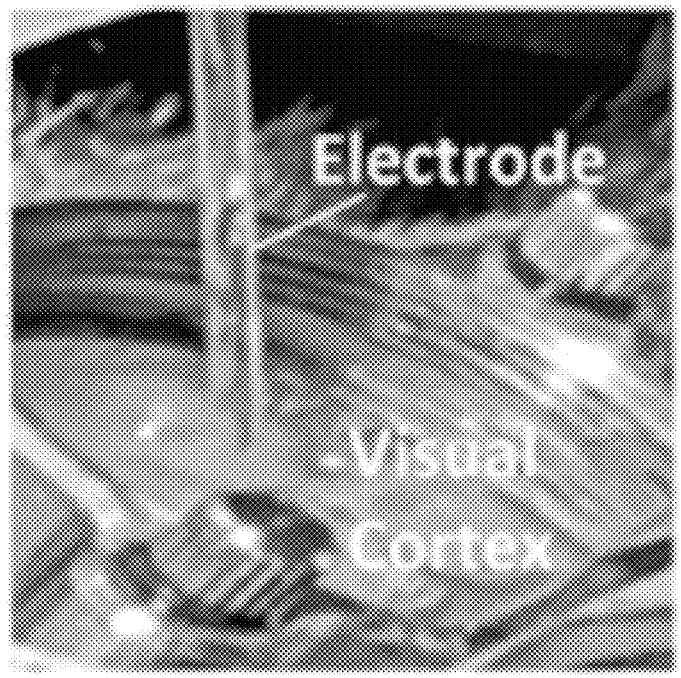
FIG. 4*e* shows D-CF electrodes that have been driven 500 μm into the cortex perpendicular to a cortical surface using a piezoelectric drive.
Figure 4F:
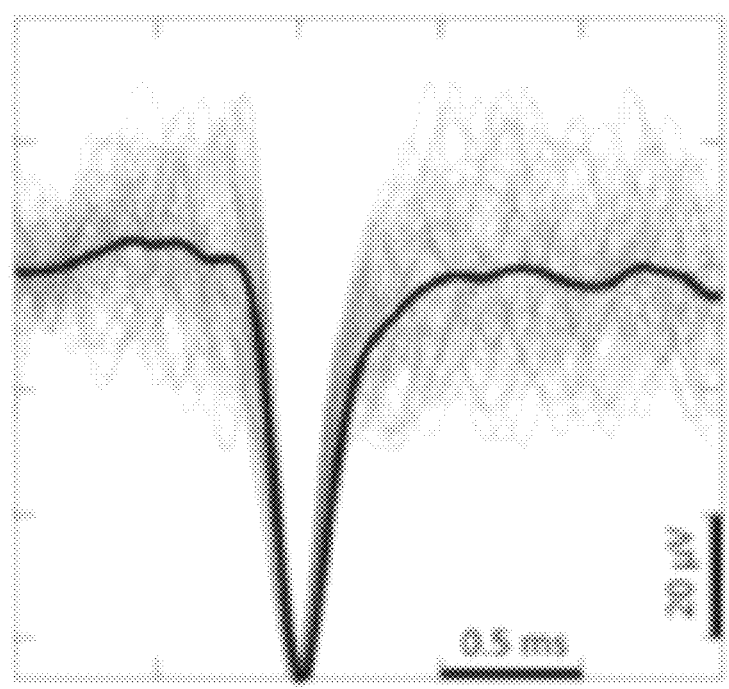
FIG. 4*f* shows spike waveforms of a single unit recorded from the visual cortex. The grey traces indicate individual spike waveforms and the black trace indicates the mean spike waveform.
Figure 4G:
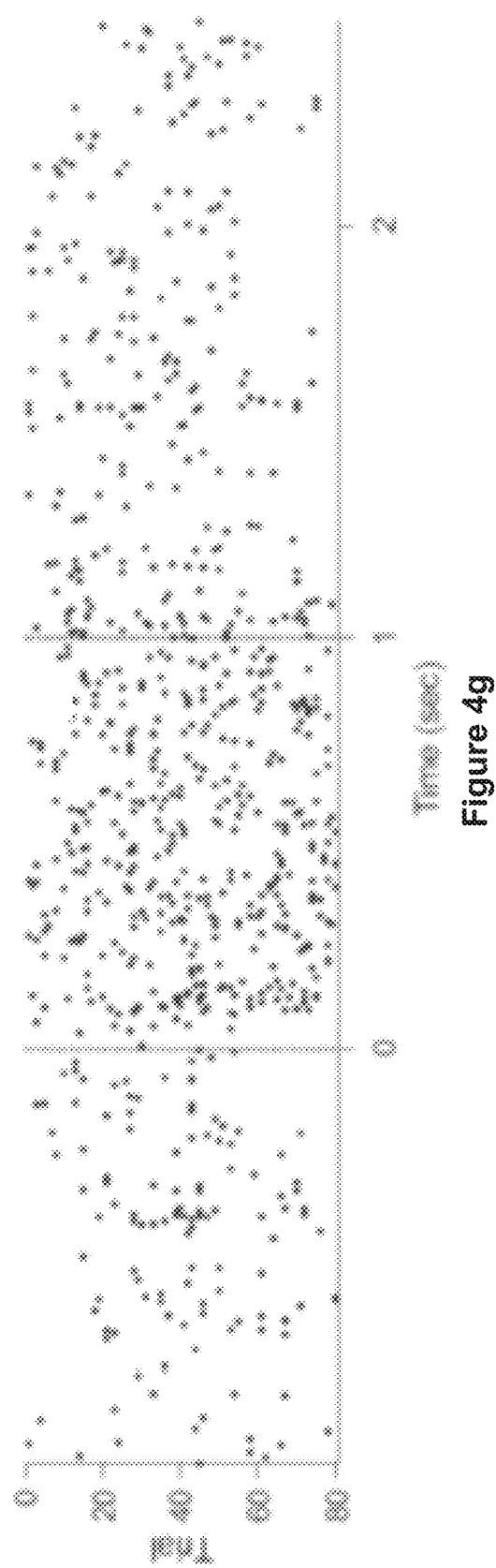
FIG. 4*g* shows a raster plot containing the responses of the single unit to eighty-six trials of a 3.5 s segment of a moving grating pattern. The red dotted lines at zero shows the onset and at 1 s the offset of the moving grating.
Figure 4H:
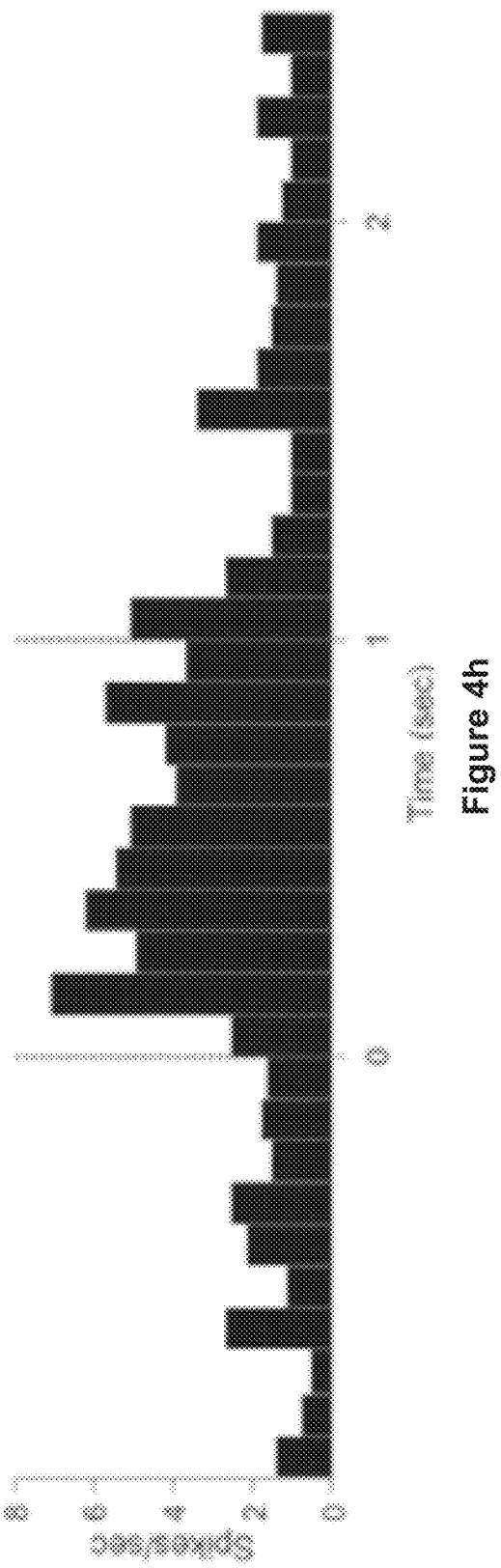
FIG. 4*h* shows a post-stimulus time histogram from the single unit with bins of 0.1 s. Time at zero is stimulus onset (first red dotted line) and stimulus offset 1 s after (second red dotted line). The X and Y axes represent time (s) and spike rate (spikes/s), respectively.

D-CF electrodes were driven 500 µm into V1 perpendicular to the cortical surface using a piezoelectric drive (FIG. 4e). This depth is suitable for investigating the primary visual cortex. Three electrodes were used in a single animal and all produced clear action potentials that could be readily extracted from the background noise, using spike sorting algorithms (FIG. 4f). To make sure that the potentials were unequivocally from visual neurons we used moving grating patterns on an LCD display to activate the visual neurons in V1. FIG. 4g shows a raster plot generated by eighty presentations of an optimally oriented grating moving through the receptive field of a V1 neuron. The moving stimulus started at time 0 and finished at time 1. Before and after the stimulus the random firing of the cell's spontaneous spikes can be readily identified. Around 0.1 s after stimulus onset there was a clear increase in spike rate, which dropped off approximately 0.1 s after stimulus offset. The timing of the response is clearly revealed by the peristimulus time histogram (FIG. 4h). In this recording, SNR (3.8) was comparable to other recording electrodes used in vivo such as parylene C coated platinum electrodes (2.77), PEDOT/CNT (3±0.6), and the electronic depth control probe (2.48±2.68).

High Sensitivity Simultaneous Dopamine and Uric Acid Detection

An important functionality of future devices will be the ability to sample chemical environments in vivo. Glucose monitors in closed-loop insulin pumps for people with diabetes are a current example of the benefit of such technologies. Dopamine (DA) is a neurotransmitter that is commonly used to evaluate a material as a neurochemical sensor and is a generic indicator of a material's ability to detect catecholamines, an important class of biomolecules. FIG. 5a shows that after electrochemical oxidation of D-CF microelectrodes, the $K_3[Fe(CN)_6]$ (ferricyanide, a generic in vitro redox test molecule) oxidation peak shifts to a higher peak voltage. This indicates an increase in carboxyl group concentration on the electrode surface. It has also been shown that oxygen-containing functional groups facilitate $Fe^{2+/3+}$ electron transfer in ferri/ferrocyanide. Oxidized diamond electrodes are also appropriate electrodes for biosensing, especially DA, an important neurotransmitter critical to our attention, learning and memory.

To infer the reproducibility of the sensor, 0.1 mM of DA was added to the electrolyte solution, and the oxidative peak current was noted during 100 cycles at a scan rate of 100 mVs-1. As shown in FIG. 5b the peak current showed a 25% decrease after 10 CVs but remained stable for subsequent 90 CVs. The kinetics of the electrochemical reactions were studied by examining the influence of scan rate on the CV redox peak current and potential of 0.1 mM DA in PBS using different voltage scan rates (FIG. 5c). A linear fit of peak current against scan rate (FIG. 5d) shows that the oxidation of DA is an adsorption-controlled process.

Analysis of CVs recorded at various concentrations of DA in 100 µM UA (in the linear range of 5-80 µM) and UA in 10 µM DA (in the linear range of 50-450 µM) (FIG. 5 e-h), demonstrates that the oxidation current of DA and UA increased linearly with concentration. Thus, selective and simultaneous detection of DA and UA was demonstrated. The detection limitation and sensitivity were 6.57 µM and 7326.04 nA µM$^{-1}$ cm$^{-2}$, respectively for DA in the presence of the high concentration (100 µM) of UA. Regardless of the effect of the surface area, the sensitivity from the slope (FIG. 5f) is 260 pA/µM. A sensitivity of 14 pA/µM was sufficient for simultaneous detection of DA and neuronal spikes using platinum electrodes in monkey brain. Hence one or more embodiments of the disclosed electrodes are well above biologically relevant sensitivity limits. Furthermore, an embodiment of a microelectrode can detect the DA peaks in the presence of high concentration UA. In contrast, prior art electrodes reported the detection of DA using CF based microelectrodes in just PBS solution. To the best of the inventors' knowledge, embodiments of the disclosure are is the first time that microelectrode-based CF has been able to detect DA in the presence of high concentrations of UA with good sensitivity and selectivity whilst still being able to stimulate tissue and record potentials. The detection limit and sensitivity were 4.53 µM and 309.94 nA pM$^{-1}$ cm$^{-2}$, respectively, for UA in the presence of 10 µM DA. In terms of stability, in vitro, the effects of oxidation of the diamond are very stable as demonstrated by long term pulsing and accelerated aging experiments.

It will be understood to persons skilled in the art of the invention that many modifications may be made without departing from the spirit and scope of the invention.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

What is claimed is:

1. A method of forming a conductive diamond layer on a surface of a carbon fiber substrate, the carbon fiber substrate coated with the conductive diamond layer configured for use as a component of an electrode for neural stimulation and/or electrochemical sensing, the method comprising:
    functionalizing at least a portion of the surface of the carbon fiber substrate with a functionalizing agent to provide a functionalized surface;
    coating the functionalized surface with diamond seeds to form a diamond seed layer covalently bonded to the functionalized surface, wherein the functionalizing agent includes a chemical moiety for forming a covalent bond between the functionalized surface and the diamond seeds; and
    using a diamond precursor, forming the conductive diamond layer via chemical vapor deposition on the diamond seed layer.

2. The method of claim 1, wherein the surface is functionalized with an amine or carboxylate group.

3. The method of claim 1, wherein the diamond seeds are bonded to the functionalized surface via an amide bond that is formed through the use of a coupling agent.

4. The method of claim 3, wherein the diamond seeds are oxygen-terminated.

5. The method of claim 1, wherein the functionalizing agent includes a diazonium moiety, wherein the step of functionalizing the at least a portion of the surface of the substrate includes applying a negative charge to the substrate to electro-catalytically convert the diazonium species to nitrogen gas and to form a covalent bond between the functionalizing agent and the at least a portion of the surface of the substrate.

6. The method of claim 1, wherein coating the at least a portion of the surface with diamond seeds to form the diamond seed layer comprises dispersing the diamond seeds in a solution to form a diamond seed solution, wherein coating the at least a portion of the surface with diamond seeds to form a diamond seed layer includes immersing the at least a portion of the surface in the diamond solution.

7. The method of claim 1, wherein the diamond seeds have a diameter ranging from about 5 nm to about 1000 nm.

8. The method of claim 1, wherein the chemical vapor deposition is microwave plasma-assisted or hot filament chemical vapor deposition.

9. The method of claim 1, wherein forming the conductive diamond layer further comprises covering at least a first portion of the surface with a mask to limit formation of the conductive diamond layer to a second portion of the surface.

10. The method of claim 9, wherein the mask is formed from a metal including molybdenum, and wherein the second portion includes a tip of the fiber.

11. The method of claim 1, wherein the diamond seed layer is uniform over the functionalized surface.

12. The method of claim 1, wherein the diamond precursor is a mixture of gases including one or more constituents containing carbon, and one or more constituents that contain nitrogen and/or boron.

13. The method of claim 12, wherein the mixture of gases includes nitrogen and the conductive diamond layer comprises a nitrogen dopant.

14. The method of claim 12, wherein the mixture of gases includes boron and the conductive diamond layer comprises a boron dopant.

15. The method of claim 1, wherein the carbon fiber substrate has a diameter>0.5 µm and the diamond seeds have a diameter of <100 nm.

* * * * *